US006271201B1

(12) United States Patent
Siler-Khodr

(10) Patent No.: US 6,271,201 B1
(45) Date of Patent: Aug. 7, 2001

(54) METHODS FOR THE SELECTIVE REGULATION OF PLACENTAL PROSTANOIDS AND INHIBITION OF LABOR USING IGF-I

(75) Inventor: Theresa M. Siler-Khodr, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 08/091,899

(22) Filed: Jul. 15, 1993

(51) Int. Cl.[7] ............................... C12N 5/02; C12N 5/08; A61K 38/30

(52) U.S. Cl. ............................... 514/12; 514/2; 514/935; 435/325; 435/366

(58) Field of Search ................. 514/2, 12, 935; 435/240.2, 240.1, 325, 366

(56) References Cited

U.S. PATENT DOCUMENTS

| | | | |
|---|---|---|---|
| 4,338,305 | 7/1982 | Corbin | 514/15 |
| 4,376,071 | 3/1983 | Jennings et al. | 530/300 |
| 4,386,160 | 5/1983 | Bramner-Jorgensen | 435/221 |
| 4,402,872 | 9/1983 | Bohn et al. | 530/369 |
| 4,415,491 | 11/1983 | Vyas et al. | 530/327 |
| 4,500,451 | 2/1985 | Bohn et al. | 530/363 |
| 4,621,055 | 11/1986 | Theurer | 435/68.1 |
| 4,622,218 | 11/1986 | Bodor | 424/9 |
| 4,732,763 | 3/1988 | Beck et al. | 424/433 |
| 4,756,907 | 7/1988 | Beck et al. | 424/433 |
| 4,945,055 | 7/1990 | Kuehl et al. | 435/226 |
| 5,168,061 | 12/1992 | Siler-Khodr | 435/219 |

FOREIGN PATENT DOCUMENTS

| | | | |
|---|---|---|---|
| 57-074087 | 5/1982 | (JP) . | |
| 58-036387 | 3/1983 | (JP) . | |
| WO92/00754 | 12/1992 | (WO) | A61K/37/36 |

OTHER PUBLICATIONS

Kang et al., "Characterization of a Placental Peptidase Which Degrades GnRH, TRH, and Angiotensin II," *Society for Gynecologic Investigation*, abstract only, Mar. 15, 1989.
Kang et al., "Characterization of the GnRH Fragments Produced by a Placental Peptidase," *The Endocrine Society*, abstract only, Jun., 1989.
Seeburg and Adelman, "Characterization of cDNA for Precursor of Human Luteinizing Hormone Releasing Hormone," *Nature*, 311:666–668, 1984.
Lee et al., "Characterization of Placental Luteinizing Hormone–Releasing Factor–Like Material," *Acta Endocrinol.*, 96:394–397, 1981.
Tan and Rousseau, "The Chemical Identity of the Immunoreactive LHRH–Like Peptide Biosynthesized in the Human Placenta," *Biochemical and Biophysical Research Communications*, 109(3):1061–1071, 1982.

Siler–Khodr et al., "Inhibition of hCG, αhCG and Progesterone Release from Human Placental Tissue in Vitro by a GnRH Antagonist," *Life Sciences*, 32:2741–2745, 1983.
Siler–Khodr et al., "Effects of a Gonadotropin–Releasing Hormone Antagonist on Hormonal Levels in the Pregnant Baboon and on Fetal Outcome," *Fertility and Sterility*, 41(3):448–454, 1984.
Gibbons et al., "In Vitro Biosynthesis of TSH– and LH–Releasing Factors by the Human Placenta," *American Journal of Obstetrics and Gynecology*, 121:127–131, 1975.
Siler–Khodr and Khodr, "Content of Luteinizing Hormone–Releasing Factor in the Human Placenta," *American Journal of Obstetrics and Gynecology*, 130(2):216–219, 1978.
Siler–Khodr and Khodr, "Extrahypothalamic Luteinizing Hormone–Releasing Factor (LRF): Release of Immunoreactive LRF in Vitro," *Fertility and Sterility*, 32(3):294–296, 1979.
Siler–Khodr et al., "Immunoreactive GnRH Levels in Maternal Circulation Throughout Pregnancy," *American Journal of Obstetrics and Gynecology*, 150:376–379, 1984.
Khodr and Siler–Khodr, "Localization of Luteinizing Hormone–Releasing Factor in the Human Placenta," *Fertility and Sterility*, 29(5):523–526, 1978.
Seppälä et al., "Immunohistochemical Demonstration of Luteinizing Hormone–Releasing Factor–Like Material in Human Syncytiotrophoblast and Trophoblastic Tumours," *Clinical Endocrinology*, 12:441–451, 1980.
Miyake et al., "Changes in Luteinizing Hormone–Releasing Hormone in Human Placenta Throughout Pregnancy," *Obstetrics & Gynecology*, 60(4):444–449, 1982.
Khodr and Siler–Khodr, "The Effect of Luteinizing Hormone–Releasing Factor on Human Chorionic Gonadotropin Secretion," *Fertility and Sterility*, 30(3):301–304, 1978.
Siler–Khodr and Khodr, "Dose Response Analysis of GnRH Stimulation of hCG Release from Human Term Placenta," *Biology of Reproduction*, 5:353–358, 1981.

(List continued on next page.)

*Primary Examiner*—Marianne P. Allen
(74) *Attorney, Agent, or Firm*—Williams, Morgan & Amerson

(57) ABSTRACT

Methods for inhibiting the production of specific vasoconstrictive prostanoids, such as thromboxane and prostaglandin $F_{2\alpha}$, through the addition of insulin like growth factor, particularly IGF-I or IGF-II, to human placental cells are disclosed. IGF-I is demonstrated to avoid affecting material and placental production of prostaglandin E, human chorionic gonadotropin, PGFM, and 6-keto-PGF1-alpha by placental cells. Improved methods for vasoregulation of vasoconstrictive diseases of pregnancy are also disclosed. Methods for treating hypertension with IGF-I are also described. Improved methods for inhibiting pre-term labor are also provided. Methods for inducing labor with agents that specifically inhibit insulin like growth factor are also disclosed. Such inhibitors of IGF-I include antibodies, antagonists of IGF-I, and metabolizing enzymes of IGF-I.

10 Claims, 11 Drawing Sheets

OTHER PUBLICATIONS

Khodr and Siler–Khodr, "Placental Leuteinizing Hormone–Releasing Factor and Its Synthesis," *Science*, 207:315–317, 1980.

Siler–Khodr and Khodr, "Production and Activity of Placental Releasing Hormones," *Fetal Endocrinology*, 183–210, 1981.

Siler–Khodr et al., "Gonadotropin Releasing Hormone (GnRH) in the Placenta," In: *Role of Peptides and Proteins in Control of Reproduction*, Dhindsa and McCann, eds., Elsevier North Holland, New York, publ., 347–363, 1982.

Siler–Khodr, "Hypothalamic–Like Releasing Hormones of the Placenta," *Clinics in Perinatology*, 10(3):553–566, 1983.

Siler–Khodr, "Hypothalamic–Like Peptides of the Placenta," *Seminars in Reproductive Endocrinology*, 1(4):321–333, 1983.

Siler–Khodr and Khodr, "Purification of Human Chorionic Gonadotropin Releasing Hormone (hCGnRH)," *Endocrinology*, 56:274 (Abstract #776), 1983.

Siler–Khodr et al., Characterization and Activity of Human Chorionic Gonadotropin Releasing Hormone (hCGnRH), *The 31st Annual Meeting of the Society for Gynecologic Investigation*, San Francisco, CA, Abstract 316:190, Mar., 1984.

Siler–Khodr et al., "Human Chorionic Gonadotropin Releasing Hormone—A Potent Stimulant of Placental Prostaglandin Production," *The 32nd Annual Meeting of the Society for Gynecologic Investigation*, Phoenix, AZ, Abstract #000:000, 1985.

Poisner et al., "Release of LHRH–Activity from Human Fetal Membranes upon Exposure to $PGE_2$, Oxytocin and Isoproterenol," *Federation Proceedings*, Abstract #1003:326, 1986.

Gautron et al., "Occurrence of Higher Molecular Forms of LHRN in Fractionated Extracts from Rat Hypothalamus, Cortex and Placenta," *Molecular Cellular Endocrinology*, 24:1–14, 1981.

Seppälä et al., "Luteinizing Hormone–Releasing Factor (LRF)–Like Immunoreactivity in Rat Pancreatic Islet Cells," *Life Sciences*, 25:1489–1496, 1979.

Seppälä and Wahlström, "Identification of Luteinizing Hormone–Releasing Factor and Alpha–Subunit of Glycoprotein Hormones in Human Pancreatic Islets," *Life Sciences*, 27:395–397, 1980.

Seppälä and Wahlström, "Identification of Luteinizing Hormone–Releasing Factor and Alpha–Subunit of Glycoprotein Hormones in Ductal Carcinoma of the Mammary Gland," *International Journal of Cancer*, 26:267–268, 1980.

Eidne et al., "Gonadotropin–Releasing Hormone Binding Sites in Human Breast Carcinoma," *Science*, 229:989–991, (1985).

Dutlow and Millar, "Rat Testis Immunoreactive LH–RH Differs Structurally from Hypothalamic LH–RH," *Biochemical and Biophysical Research Communications*, 101(2):486–493, 1981.

Bhasin et al., "Partial Isolation and Characterization of Testicular GnRH–Like Factors," *Endocrinology*, 112(3):1144–1146, 1983.

Sokol et al., "Hormone–Like Factors in Human Seminal Plasma," *Biology of Reproduction*, 33(2):370–374, 1985.

Hersh and McKelvy, "Enzymes Involves in the Degradation of Thyrotropin Releasing Hormone (TRH) and Luteinizing Hormone Releasing Hormone (LH–RH) in Bovine Brain," *Brain Research*, 168:553–564, 1979.

Chertow, "The Role of Lysosomes and Proteases in Hormone Secretion and Degradation," *Endocrine Reviews*, 2(2):137–173, 1981.

Mizutani et al., "Post–Proline Endopeptidase in Human Placenta," *Biochemica et Biophysica Acta*, 786:113–117, 1984.

Johnson et al., "Enzymes in Placental Microvilli: Angiotensin I Converting Enzyme, Angiotensinase A, Carboxypeptidase, and Neutral Endopeptidase ("Enkephalinase")," *Peptides*, 5(4):789–796, 1984.

Kenny et al., "Dipeptidyl Peptidase IV, a Kidney Brush-–Border Serine Peptidase," *Biochem. J.*, 155:169–182, 1976.

Kang et al. "Dose–Related Action of Gonadotropin–Releasing Hormone on Basal Prostanoid Production from the Human Term Placenta," *American Journal of Obstetrics and Gynecology*, 165(6):1771–1776, 1991.

Siler–Khodr and Forman, "Dose–Related Action of IGF–I on Placental Prostanoid Release," *The 26th Annual Meeting of the Society for the Study of Reproduction* (Ft. Collins), Abstract #479:178 (1993).

Siler–Khodr and Forman, "IGF–I Inhibits Human Placental Prostaglandin F and Thromboxane $B_2$ Production," *The 38th Annual Meeting of the Society for the Study of Reproduction* (Raleigh, NC), Abstract #513:178 (1992).

Murphy and Ghahary, "Uterine Insulin–Like Growth Factor–1: Regulation of Expression and Its Role in Estrogen–Induced Uterine Proliferation," *Endocrine Reviews*, 11(3):443–453, 1990.

Goodman and Gilman's, "The Clinical Use of Drugs That Inhibit Uterine Motility," *The Pharmacological Basis of Therapeutics*, Eighth Edition, Pergamon Press, New York, NY, chap. 39, pp. 949–953 (1990).

Mentlein and Heymann, "Dipeptidyl Peptidase IV Inhibits the Polymerization of Fibrin Monomers," *Chemical Abstracts*, 15:122, Abstract No. 97:122831v, 1982.

Kang et al., "Effect of Exogenous Arachidonic Acid and Enzyme Inhibitors on Placental Prostanoid Production," *Placenta*, 14:341–353 (1993).

Pueschel et al., "Isolation and Characterization on Dipeptidyl Peptidase IV from Human Placenta," *European Journal of Biochemistry*, 126(2):359–365, 1982, abstract only.

Suzuki, "Studies on Mode of Cystine Aminopeptidase Production in the Human Placental Chorionic Villi and Its Effect on Angiotensin II During Pregnancy," *Acta Obstetrica et Gynaecologica Japonica*, 37(10):2039–2048, 1985, abstract only.

Mizutani et al., "Purification and Properties of Human Placental Dipeptidyl Peptidase IV," *Chemical Abstracts*, 103:198, 1985, Abstract #33917C.

The Merck Index, Eleventh Edition, Susan Budavari, Ed., Merck & Co., Inc., Rahway, NJ, publ., pp. 1104 and 1562, 1989.

Kang et al., "Definition of the Enzyme Kinetics and Optimal Activity of Chorionic Peptidase–1," *Society for the Study of Reproduction*, abstract only (1990).

Siler–Khodr et al., "Characterization and Purification of a Placental Protein That Inactivates GnRH, TRH and Angiotensin II," *Placenta*, 10(3):283–296, 1989, abstract only.

Petraglia et al., "Localization, Secretion, and Action on Inhibin in Human Placenta," *Science*, 237:187–189, 1987.

Siler–Khodr et al., "Differential Inhibition of αhCG, hCG, Progesterone, Estrogens and Prostaglandins from Early and Midgestational Human Placental Cultures by a GnRH Antagonist," *Society for Gynecologic Investigation,* 30th Annual Meeting, Washington, D.C., Mar., 1983, Abstract #6.

Siler–Khodr et al., "Hormonal Response to GnRH in Vitro for Human Placentas of Different Gestational Ages," *Society for Gynecologic Investigation,* 30th Annual Meeting, Washington, D.C., Mar., 1983, Abstract #5.

Siler–Khodr et al., "Levels of GnRH in Maternal Circulation During Pregnancy," *Society for Gynecologic Investigation,* 30th Annual Meeting, Washington, D.C., Mar., 1983, Abstract #4.

Curtis and Fink, "A High Molecular Weight Precursor of Luteinizing Hormone Releasing Hormone from Rat Hypothalamus," *Endocrinology,* 112:390–392, 1983.

Khodr and Siler–Khodr, "Synthesis of LRF by Human Placenta in Vitro and Stimulation of hCG Release by Synthetic LRF," *Society for Gynecologic Investigation,* 26th Annual Meeting, San Diego, CA, Abstract #141:85, 1979.

Siler–Khodr et al., "LRF Stimulation of Chorionic Gonadotropin and Estrogen Release in the Pregnant Monkey," *Endocrinology,* 104:A–122, Abstract #199, 1979.

Khodr and Siler–Khodr, "Studies of Luteinizing Hormone Releasing Factor (LRF) in the Human Placenta," *Society for Gynecologic Investigation,* 25th Annual Meeting, Atlanta, GA, Abstract #3:2, 1977.

Siler–Khodr and Khodr, "Characterization of Endogenous Human Chorionic GnRH and the Effects of GnRH on Placental Hormone Levels," *Society for Gynecologic Investigation,* 28th Annual Meeting, St. Louis, MO, Abstract #240:142, 1981.

Siler and Siler–Khodr, "Studies of LRF in Pregnancy: Levels in Maternal, Placental, Amniotic and Fetal Tissues," *Endocrinology,* 100:A–354, Abstract #583, 1977.

Millar et al., "Stimulation of Gonadotropin Release by a Non–GnRH Peptide Sequence of the GnRH Precursor," *Science,* 232:68–70, 1986.

Siler–Khodr and Khodr, "More Evidence on Production of LRF by Human Placenta," *Modern Medicine,* pp. 156, Jun. 15–30, 1978, abstract only.

Siler–Khodr et al., *Prostaglandins,* 46:361–370, Oct. 1993.*

Geisthovel, F. et al., *Human Reproduction,* 5(7):785–99, 1990.*

Johnson, *Am J. Obstr Gynecol.,* 123(4):364–375, 1975.*

Vane, *Br. J. Pharmacol.,* 48(4):629–39, 1973.*

* cited by examiner

METHODS FOR THE SELECTIVE REGULATION OF PLACENTAL PROSTANOIDS AND INHIBITION OF LABOR USING IGF-I

The United States government may have rights in the present application as research relevant to the development of the invention was supported by NIH grant 21708 and HD 10202.

BACKGROUND OF THE INVENTION

Nearly 11% (approximately 225,000 a year) of all pregnancies in the United States result in pre-term delivery. Such results in a significant incidence of perinatal morbidity and mortality. Despite major advances in neonatal care, retention of the fetus in utero is preferred in most instances. However, the desire to prolong intrauterine development must be balanced against the risks of continued pregnancy to both the mother and fetus, as well as the risks of concurrently available forms of pharmacological intervention. In general, the use of tocolytic agents to prolong pregnancy is reserved for those cases where the gestational age is greater than 20 weeks and less than 34 to 36 weeks.

There are several indications for, and contraindications to, the clinical use of agents that inhibit labor by inhibiting uterine contractions. The clearest indications for such agents are (1) to delay or prevent premature parturition in selected individuals and (2) to slow or arrest delivery for brief periods in order to undertake other therapeutic measures. Tocolytic agents that are currently in use for inhibiting contractions include $\beta_2$-adrenergic agonists, magnesium sulfate, ethanol, and inhibitors of prostaglandin synthesis, such as indomethacin. The use of tocolytic agents has been reviewed in several symposia (Symposium, 1981, 1982) and by Caritis (1983).

In the current practice of obstetrics, the use of indomethacin, which is an enzyme inhibitor, to inhibit prostaglandins in the treatment of premature labor prior to 33 weeks of gestation, is an accepted medical practice. However, enzyme inhibitors of prostaglandin synthesis, such as indomethacin, can unnecessarily prolong gestation in term pregnancies. In addition, the use of indomethacin in premature labor has been curtailed because of concern for its potential for causing adverse effects in the fetus. of particular importance is the possibility of premature closure of the ductus arteriosus and the production of pulmonary hypertension from use of indomethacin. In addition, relatively high molar concentrations of indomethacin are necessary to produce pharmacological affects, on the order to at least $10^{-3}$ molar (M).

For example, the indiscriminate inhibition of several vasodilatory and vasoconstrictive prostanoids by indomethacin (prostaglandin $E_2$, prostaglandin $F_{2\alpha}$, prostacyclin, thromboxane $A_2$) is believed to be related to the incidence of serious complications to mother and fetus from the use of this agent in vivo. For example, inhibition of prostacyclin in the pregnant animal can result in vasoconstriction; while inhibiting PGE can result in premature closure of the fetal ductus arteriosus. While fetal echocardiography can detect early signs of constriction of the ductus arteriosus, and its use may permit the continued administration of indomethacin or related agents in those instances where evidence of ductal construction is absent (Moise et al., 1988), the risk of these serious side effects make the treatment undesirable. The potentially serious side affects observed with currently employed regimens for managing labor, particularly with the use of indomethacin through the control of prostaglandin synthesis, continues to prompt research efforts to identify the mechanisms involved in the onset and progression of labor.

Prostanoids are a family of autacoids (formed from arachidonic acid) thought to play an important role during implantation, in the progress and maintenance of pregnancy, and during the initiation and progress of labor (Angle and Johnston, 1990). Placental prostanoid production is considered to be important during labor as well as throughout pregnancy, in regulating vascular tone, as well as affecting other hormonal production (Myatt, 1990). In human pregnancy, multiple sites of chorionic prostanoid production have been identified, i.e., the anion, the chorion, the decidua and the placenta (Duchesne et al., 1978; Mitchell et al., 1978a, 1978b, 1978c; Robinson et al. 1979; Haning et al., 1982; Olson et al., 1983; Harper et al., 1983; Siler-Khodr et al., 1986b). In addition to its role in prostanoid production, the placenta also has multiple paracrine and endocrine capacities in human pregnancy. Although it is recognized that prostanoids such as prostaglandin $E_2$, prostaglandin $F_{2\alpha}$, the metabolite of $PGF_{2\alpha}$, 13,14-dihydro-, 15-keto-prostaglandin $F_{2\alpha}$ (PGFM), thromboxane $A_2$ ($TxB_2$) and prostacyclin ($PGI_2$) are all produced by placental tissue, the quantities of these substances, relative to the size of the placenta is frequently not appreciated. In addition, while the placenta is known to be an important site of prostanoid production, little is known of factors controlling the production of these prostanoids from human placental tissues.

Abnormal placental prostanoid production has been reported in diseases of pregnancy, including pregnancy-induced hypertension and intra-uterine growth retardation (Demers and Gabbe, 1976; Robinson et al., 1979; Hillier and Smith, 1981; Valenzuela and Bodhke, 1980; Jogee et al., 1983; Walsh, 1985). However, very few studies have been done on the control of human placental prostanoid release.

Insulin like growth factor (IGF-I), also commonly known as somatomedin-C, is a growth factor that is well known for its stimulation of cellular proliferation, and is recognized as the principal mediator of the action of growth hormone. (Murphy et al. (1990), Endocrine Reviews, 11(3): 443–453)). The IGFs are known to circulate in relatively high concentrations in the body, despite the fact that they are synthesized in many, if not most, tissues. The known activity of IGF-I in mediating growth hormone is consistent with the observation made by others that it may enhance fetal growth. IGF-I, however, has not been described as important in the onset or during the progression of labor, and therefore, the use of IGF-I during labor has not been examined. Nor has IGF-I been described as related to the activity of prostaglandins or prostanoids.

SUMMARY OF THE INVENTION

The present invention provides improved methods for managing pre-term labor, as well as for inducing labor, in for example post-term pregnancies, without the potential for risk to the fetus or mother associated with use of other common pharmaceutically used drugs that modulate prostaglandin production, such as indomethacin.

Insulin like growth factor I (IGF-I) is a hormone that is demonstrated by the present inventor to be particularly useful at relatively low molar concentrations, on the order of $10^{-9}$ molar, in producing a selective pharmacological affect on human placental tissue.

More specifically, IGF-I is demonstrated to provide a specific and effective inhibition of the production of particular vaso-constrictive chorionic prostanoids, particularly thromboxane and prostaglandin $F_{2\alpha}$ by human placental cells, without inhibiting the production of vasodilating prostanoids, such as prostacyclin ($PGI_2$) or prostaglandin $E_2$. The disadvantages of non-specific inhibition of prostaglandin $E_2$ and high pharmacologically effective molar concentrations associated with the use of enzyme inhibitors, such as indomethacin and indomethacin-like analogs are therefore avoided. The methods may be used for regulating the production of vasoconstrictive prostanoids from chorionic tissues, such as the anion, the chorion and the placenta. In addition, analogs of IGF-I and IGF-II are anticipated to provide the specific prostanoid regulation from chorionic tissues in conjunction with the claimed invention.

In one aspect of the present invention, a method for selectively regulating chorionic cell, particularly placental cell, production of thromboxane and prostaglandin $F_{2\alpha}$ is provided. The method most preferably comprises treating placental cells with a pharmacologically effective amount of insulin like growth factor (IGF-I) or an analog thereof. For purposes of describing the present invention, a pharmacologically acceptable concentration of IGF-I is defined as an amount sufficient to inhibit thromboxane and prostaglandin $F_{2\alpha}$ production by placental cells without inhibiting or otherwise affecting placental prostaglandin $E_2$ or prostacyclin (PGI) production. While inhibition of thromboxane and prostaglandin $F_{2\alpha}$ production will occur upon treatment with IGF-I, production of prostaglandin $E_2$, human chorionic gonadotropin and PGFM will remain unaffected.

It is anticipated that either IGF-I, IGF-II, or analogs of these agents, may be employed in the described methods. However, IGF-I is most preferred. The described method may be employed to regulate production of chorionic thromboxane and $PGF_{2\alpha}$ in any variety of placental cells, such as those of farm or domesticated animals or humans. In a most preferred embodiment, the claimed method provides for the regulation of human chorionic tissue prostanoid production, particularly by human placental cells.

In this particular aspect of the invention, a pharmacologically effective concentration of insulin like growth factor, particularly IGF-I, effective to inhibit thromboxane production by human placental cells in vivo is defined as an amount sufficient to achieve a concentration of between about $10^{-7}$ to about $10^{-10}$. This amount constitutes a pharmacologically active dose that is well within physiological ranges, and therefore can be readily used by the artisan of ordinary skill in pharmacy as a basis for defining an appropriate dose to be used in vivo as part of an appropriate human dose regimen.

In still another embodiment of the invention, a method for inhibiting labor by inhibiting the production of thromboxane and prostaglandin $F_{2\alpha}$ by placental cells is provided. The method most preferably comprises administering to a pregnant animal a pharmacologically effective amount of insulin like growth factor sufficient to inhibit the production of thromboxane ($TxB_2$) and prostaglandin $F_{2\alpha}$ by chorionic cells without affecting prostacyclin, prostaglandin E, PGFM, and human chorionic gonadotropin (hCG) production.

While the claimed method may be useful in the treatment of any variety of animals, the present inventor contemplates the particular utility of the method in the treatment of premature labor in humans. Specifically, spontaneous labor prior to between about 20 and about 34 weeks gestation in a pregnant human female may be inhibited employing the present method by administering a pharmacologically effective dose of a clinical grade insulin like growth factor I (IGF-I) to the patient. Clinical grade insulin like growth factor (IGF-I or IGF-II), particularly IGF-I and IGF-II made by recombinant techniques are available from pharmaceutical suppliers, such as for human use. The dose of insulin like growth factor to be administered to the patient will vary depending upon the particular circumstances of the patient being treated, for example, the mode or delivery (vaginal, C-section), the weight of the pregnant female, and the particular gestational age of the fetus. The IGF-I or IGF-II would be given to the patient until clinical indications of the labor subsiding, such as cessation of contractions or halted cervical dilation and effacement is observed by the attending physician. These parameters are well known to those of skill in the obstetrical arts, as is the determination of appropriate doses to administer to a patient given the disclosure provided herein.

It is contemplated that a pharmacologically effective amount of insulin like growth factor, IGF-I, sufficient to inhibit thromboxane production by placenta in a pregnant human female will generally be an amount sufficient to achieve a concentration of between about 5 ng/ml to about 80 ng/ml in the anionic fluid surrounding the fetus or umbilical cord blood of the fetus. Insulin like growth factor may be administered to the patient by any variety of routes, for example, subcutaneously, intramuscularly, intravenously, or intra-anionically. Most preferably, the insulin like growth factor is to be administered to the patient intra-anionically. The insulin like growth factor-I (IGF-I) may be administered to the patient as it is obtained from the pharmaceutical supplier in a pharmaceutically acceptable carrier solution, or may be diluted to a desired dosage with pharmaceutically acceptable carrier solutions generally available from pharmaceutical suppliers. Clinical grade preparations of IGF-I and IGF-II are available for use in humans in conjunction with the practice of the present invention.

The present disclosure also provides a method for inducing labor in a pregnant animal. According to one embodiment of the method, labor is to be induced by inhibiting IGF-I in the animal, which would be expected to result in a concomitant increase in the production of thromboxane and $PGF_{2\alpha}$ from chorionic tissues, particularly placental cells. The present inventor contemplates that these physiological events may be accomplished by administering a pharmacologically effective amount of a specific inhibitor of insulin like growth factor-I (IGF-I) or insulin like growth factor-II (IGF-II) to the pregnant animal.

By way of example, specific inhibitors of insulin like growth factor IGF-I or IGF-II include antibodies having specific binding affinity for IGF-I or IGF-II. While both polyclonal and monoclonal antibodies may be employed for such use, monoclonal antibodies are most preferred. By way of example, a monoclonal antibody specific for IGF-I may be prepared according to standard hybridoma preparation techniques as outlined in the present disclosure. Other specific inhibitors of insulin like growth factor that are contemplated by the present inventors to be useful in the described method for inducing labor include synthetic antagonists of IGF-I or IGF-II, and metabolizing enzymes of IGF-I or IGF-II. Specific inhibitors of IGF-I may be administered to an animal through any variety of routes, including subcutaneous, intramuscular, or intravenous administration, as described above.

In practice, the attending physician would administer an inhibitor of insulin like growth factor (such as IGF-I, IGF-II) to a pregnant female of at least 40 weeks gestational age, or to a female of lesser gestational age medically where indicated, and continue to administer the IGF-I or IGF-II inhibitor until clinically recognized symptoms of the onset of labor are observed, such as the onset of contractions or dilation of the cervix effacement.

It is anticipated that the described method may be particular efficacious in the treatment of pregnant human females having progressed beyond about 42 weeks gestational age, or in those situations where the induction of labor is otherwise medically indicated for the safety of the mother and/or child. Again, the specific inhibitor of insulin like growth factor would be administered to the pregnant female until contractions commence and/or until the observation of other clinically recognized signs of labor onset, such as dilation of the cervix or effacement.

Standard gynecological and obstetrical clinical procedures well known to those of skill in the obstetrical art would be employed in the application of the herein disclosed methods for both inhibiting and inducing labor, as well as in the treatment of gestational hypertension, given the present disclosure of the specific activity of the insulin like growth factor I on human placental cells, and the specific inhibitory effect that IGF-I and IGF-II inhibitors are anticipated to have on chorionic tissue prostanoid production.

The present invention also provides methods for regulating vasoconstriction through the administration of insulin like growth factor, such as IGF-I or IGF-II, or analogs thereof. IGF-I is most particularly preferred for this use. This method would be particularly efficacious for the treatment of gestational hypertension in a pregnant human female. Again, the specific inhibitory activity of IGF-I on placental tissue production of vasoactive prostanoids, such as thromboxane and prostaglandin $F_{2\alpha}$, provides a potentially powerful clinical tool in the management of this pathology without the undesirable side effects associated with other non-specific prostanoid inhibitors.

The following abbreviations are employed throughout the description of the present invention:

| | |
|---|---|
| DMSO = | Dimethyl sulfoxide |
| PGE = | prostaglandin E |
| 6-Keto – $PGF_{1\alpha}$ = | 6-keto prostaglandin $F_{1\alpha}$ |
| PGFM = | 13, 14,-dihydro-15 keto-prostaglandin F |
| BSA = | Bovine serum albumin |
| EDTA = | ethylene diamino tetraacetia acid |
| U = | Units |
| $TxB_2$ = | Thromboxane $B_2$ |
| IGF-I = | Insulin like growth factor-I |
| PGF = | prostaglandin F |
| PGI = | prostacyclin |
| NDGA = | Nordihydroguaiaretic Acid |

DETAILED DESCRIPTION OF THE PREFERRED EMBODIMENTS

Figure 1:
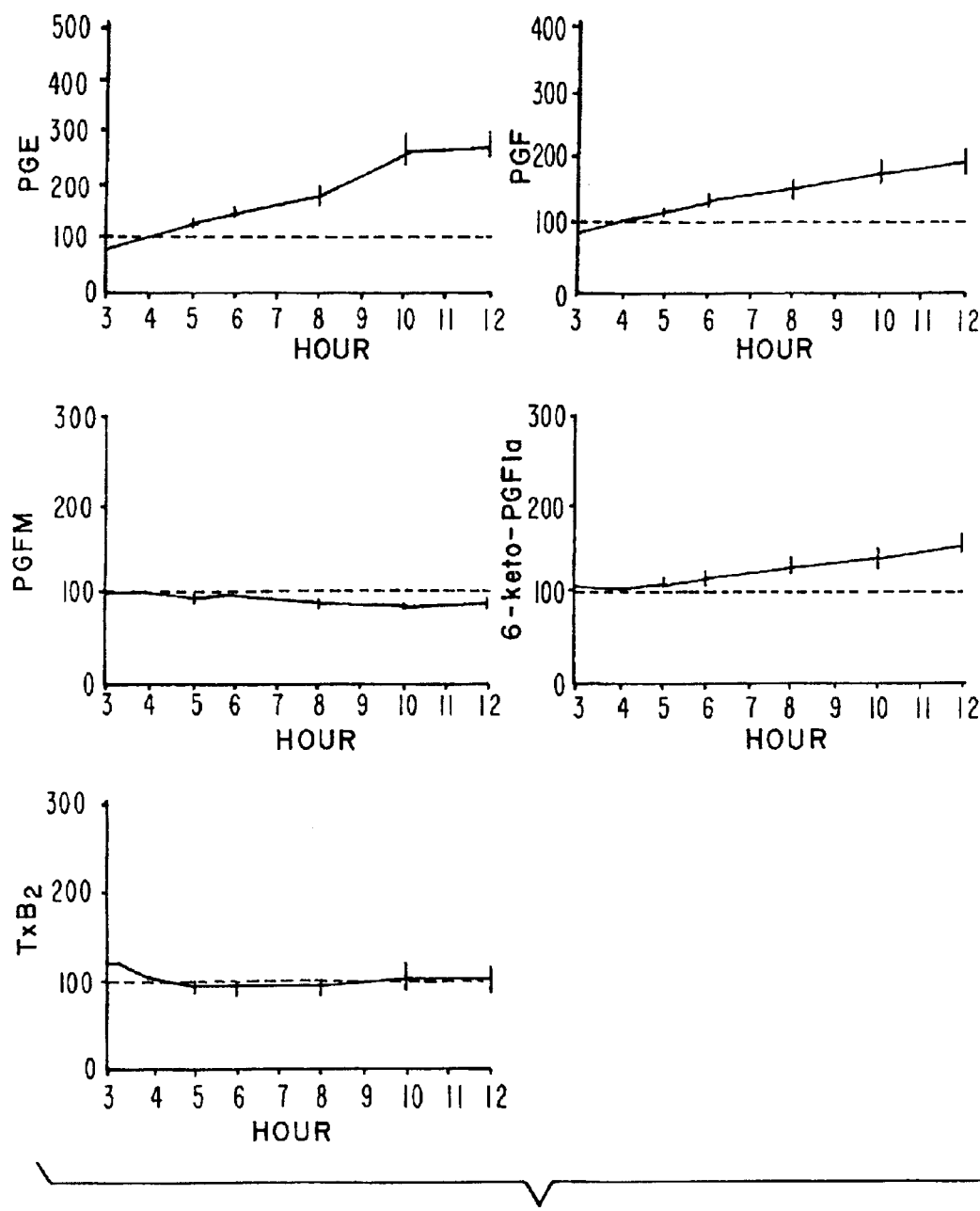
FIG. 1. Prostanoid release, normalized to the fourth hour release, of PGE, PGF, PGFM, 6-keto-$PGF_{1\alpha}$ and $TxB_2$ from human term placenta (mean±SEM).

Methods for selectively regulating the production of prostanoids from chorionic tissues, particularly placental tissue are provided. Chorionic production of thromboxane $B_2$ and prostaglandin $F_{2\alpha}$ is regulated (inhibited) without significant effects on prostaglandin $E_2$ or prostacyclin production by placental cells by administering a pharmacologically effective dose of IGF-I, IGF-II, or analog thereof. The methods also include improved strategies for managing pre-mature labor by use of IGF-I, IGF-II, or analogs thereof. Techniques for inducing labor in an animal are also provided by decreasing IGF-I in an animal, by, for example, administering a specific inhibitor of IGF-I or IGF-II.

Amounts of prostacyclin (PGI) were determined as a measure of 6-keto-$PGF_{1\alpha}$. 6-keto-$PgF_{1\alpha}$ is the immediately formed metabolite of the active molecule PGI (see FIG. 7), and thus provides an accurate measure of PGI amounts.

Amounts of thromboxane A were determined as a measure of thromboxane $B_2$. Thromboxane A is converted almost instantaneously to thromboxane $B_2$, and therefore constitutes a well accepted measure of thromboxane $B_2$ by those of ordinary skill in the art.

Recombinant IGF-I was purchased from Chemicon International, Inc. (Terecula, Calif.). Clinical grade IGF-I may be obtained from Chemicon International, Inc., Terecula, Calif., that sells a recombinant form of IGF-I that may be formulated according to standard pharmaceutical techniques to provide a preparation particularly suitable.

Even though the invention has been described with a certain degree of particularity, it is evident that many alternatives, modifications, and variations will be apparent to those skilled in the art in light of the foregoing disclosure. Accordingly, it is intended that all such alternatives, modifications, and variations which fall within the spirit and the scope of the invention be embraced by the defined claims.

The following examples are presented to describe preferred embodiments and utilities of the present invention, but should not be construed as limiting the claims thereof.

EXAMPLE 1

Radioimmunoassays

The present example describes the various assays and materials used by the inventor in the characterization of chorionic, particularly placental, tissue response to IGF-I.

Prostanoid Radioimmunoassays

Radioimmunoassays were performed in a fashion similar to what has been previously described (Siler-Khodr et al., 1986, Biol. Reprod., 35:312) which is specifically incorporated herein for this purpose, with specific exception as noted below. A perifusion model (described in Examples 2 and 3) was employed to determine placental cell response. Media collected from the perifusion samples prepared from placental tissues were assayed. After an initial pilot study of the prostanoid release of each of the perifusion placental tissue media samples collected hourly, samples from hours 3, 4, 5, 6, 8 and 12 of the perifusion were chosen for assay and for data analysis. All the samples from a given perifusion (placenta) were determined in the same assay.

PGE—A specific antiserum for PGE (both 1 and 2, 50% and 100%, respectively) obtained from Advanced Magnetics, Inc. (Cambridge, Mass.) was used at a final dilution of 1/37,500. Label [5,6,8,11,12,14,15(n)-$^3$H]-PGE$_2$, which was purchased from Amersham Corp. (Arlington Heights, Ill.), was added to every tube (25 pg). Assay sensitivity was 8 pg/tube and the intra- and interassay coefficients of variation were 7.8% and 9.8%, respectively. The only cross-reactivities greater than 1% were PGA$_2$, 6%; PGA$_1$, 30%; and PGF$_{2\alpha}$, 1.3%.

PGF—A specific antiserum for PGF prostaglandins obtained from Advanced Magnetics, Inc. was used at a final dilution of 1/60,000. Label [5,6,8,9,11,12,14,15(n)-$^3$H]-PGF$_{2\alpha}$, which was purchased from Amersham Corp., was added to every tube (25 pg). Assay sensitivity was 1.5 pg/tube and the intra- and interassay coefficients of variation were 11.0% and 10.4%, respectively. The only cross-reactivities greater than 1% were PGE$_1$, 1.1%, 6-keto-PGF$_{1\alpha}$, 1.1%; TxB$_2$, 0.5%; and PGE$_2$, 0.3%.

PGFM—A specific antiserum to PGFM was obtained from Advanced Magnetic, Inc. and used at a final dilution of 1/4,000. Label [5,6,8,9,11,12,14(n)-$^3$H]-13,14-dihydro-15-keto-PGF$_{2\alpha}$, which was purchased from Amersham Corp., was added to every tube (25 pg). Assay sensitivity was 7 pg/tube and the intra- and interassay coefficients of variation were 10.2% and 9.6%, respectively. The only cross-reactivities greater than 0.1% were PGF$_{2\alpha}$, 1.7% and 13,14-dihydro-15-keto-PGE$_2$, 0.14%.

TxB$_2$—A specific antiserum to TxB$_2$ was obtained from Advanced Magnetic, Inc. (Cambridge, Mass.) and used at a final dilution of 1/70,000. Label [5,6,8,9,11,12,14(n)-$^3$H]-TxB$_2$, which was purchased from Amersham Corp. (Arlington Heights, Ill), was added to every tube (25 pg). Assay sensitivity was 1.7 pg/tube and the intra- and interassay coefficients of variation were 5.3% and 5.7%, respectively. There were no cross-reactivities greater than 0.1%.

6-keto-PGF$_{1\alpha}$—A specific antiserum to 6-keto-PGF$_{1\alpha}$ was obtained from Advanced Magnetics, Inc. and used at a final dilution of 1/137,500. Label [5,6,8,9,11,12,14(n)-$^3$H]-6-keto-PFG$_{1\alpha}$, which was purchased from Amersham Corp. (Arlington Heights, Ill.), was added to every tube (25 pg). Assay sensitivity was 7 pg/tube and the intra- and interassay coefficients of variation were 8.6% and 7.4%, respectively. The only cross-reactivities greater than 0.01% were PGF$_{1\alpha}$, 7.8%, 6-keto-PGE$_1$, 6.8%; PGF$_{2\alpha}$, 2.2%; PGE$_1$, 0.7%; PGE$_2$, 0.6%.

hCG—A specific antiserum to hCG was obtained from Advanced Magnetic, Inc. and used at a final dilution of 1/500,000. Radio-iodinated hCG (CR-119) (500 pg) having a specific activity of 350 $\mu$Ci/$\mu$g was added to every tube. Assay sensitivity was 1.7 pg/tube and the intra- and interassay coefficients of variation were 5.3% and 5.7%, respectively. There were no cross-reactivities greater than 0.1%.

Dexatmethasone was obtained from Sigma Chemical Company.

Arachdemie Acid was obtained from Sigma Chemical Co.

IGF-I was obtained from Chemicon International, Inc. in Temecula, Calif.

Prostanoid Recovery and Stability

Samples were stored at −20° C. until assayed for PGE, PGF, PGFM, TxB$_2$ and 6-keto-PGF$_{1\alpha}$. Recovery and stability of these prostanoids in the perifusion system used in the present studies and during storage was assessed by spiking the medium with prostanoids and perifusing it through empty chambers and collecting samples as described above. In addition, samples were frozen and thawed repeatedly and re-assayed.

Prostanoid recovery and stability in the systems described illustrating the present invention were nearly 100%. PGE, PGF, PGFM, TxB$_2$, and 6-keto-PGF1$\alpha$ were obtained from the sources previously described herein, as well as characterized in and between assays as described.

EXAMPLE 2

Effect of Enzyme Inhibitors on Placental Prostanoid Release

The effect of enzyme inhibitors, including indomethacin quinacrine, EDTA, NDGA and Ca$^+$ chelator, on basal prostanoid release by human placental cells is provided in the present example. Radioimmunoassay was conducted as described in Example 1.

At the beginning of the fifth hour of the perifusion, Medium 199 in the experimental chambers was changed to Medium 199 containing quinacrine (10 $\mu$M), EDTA (1 mM), NDGA (10 $\mu$M) or indomethacin (50 $\mu$g/ml). Four replicated chambers were perifused with control medium and each of the experimental media. This experimental design was repeated in three different perifusions using placental tissues from three different patients according to the procedure described in Example 3. Incubation with indomethacin resulted in an immediate inhibition of PG, PGF, TxB$_2$ and 6-keto-PGF$_{1\alpha}$, with a delayed inhibition of PGFM.

Prostanoid Recovery and Stability

Samples were stored at −20° C. until assayed for PGE, PGF, PGFM, TxB$_2$ and 6-keto-PGF$_{1\alpha}$. Recovery and stability of these prostanoids in the perifusion system used in the present studies and during storage was assessed by spiking the medium with prostanoids and perifusing it through empty chambers and collecting samples as described above. In addition, samples were frozen and thawed repeatedly and re-assayed. Prostanoid recovery and stability was nearly 100%.

Placental Perifusion

Term placentas were obtained and placed on ice immediately after vaginal delivery from patients having spontaneous labor and delivery without any known obstetrical or medical complications. Tissues were obtained in accordance with a protocol approved by the Institutional Review Board. Within 30 minutes, the placental tissues were dissected of decidua, chorionic plates and large fetal vessels on ice. The placental tissues were cut into small fragments (approximately 25 pieces having a total weight of approximately 1 g), rinsed free of blood by repeated washing with ice cold normal saline until clear in color, and the tissue fragments placed in a 3-ml tissue chamber, placed in a 37° C. water bath. Twenty replicate chambers were prepared and each perifused with Medium 199 containing 0.05% BSA, 100 U penicillin and 100 $\mu$g streptomycin per ml at a rate of 1 ml per hour for 12 hours. This medium is hereafter referred to as Medium 199. The influx medium was aerated with 95% air and 5% $CO_2$ throughout the perifusion. Perifusion was performed for two hours prior to initiation of sample collection. In this fashion, all tissues were thoroughly washed and equilibrated. Samples were collected hourly, beginning at the start of the third hour, into 12×75 mm glass tubes containing 0.1 ml indomethacin and 1100 $\mu$g/ml dimethyl sulfoxide [DMSO]. It took approximately one hour for the input medium to pass through the perifusion tubing and chamber and to be collected in the sample tube, thus the dead volume of the system was approximately 1 ml. Collection of the effluent of the 20 chambers was done simultaneously, using an ISCO fraction collector Retriever III adapted with a 20-tube rack and manifold.

Materials

Medium 199 (×2) with Earles' Modified Salts, bicarbonate and L-glutamine without phenol red was purchased from Gibco Laboratories (Chargin Falls, Ohio). Penicillin, streptomycin and bovine serum albumin were obtained from Sigma Chemicals (St. Louis, Mo.). Quinacrine, NDGA, EDTA and indomethacin were also purchased from Sigma Chemicals. IGF-I was purchased from Chemicon International, Inc. (Terecula, Calif.).

Basal Placental Prostanoid Release

The basal (control) release (mean±SEM) of PGE, PGF, PGFM, 6-keto-$PGF_{1\alpha}$, and $TxB_2$ per mg wet weight of tissue from seven placentas, from the third to the 12th hour of perifusion, is given in Table 1. The coefficient of variation within and between placentas was as much as 40% when release rate per mg of tissue was analyzed. However, if the release in a given perifusion chamber is normalized to the fourth-hour release for that chamber, and the mean of the four replicate chambers of each given placenta then determined, the variation between chambers for the given placenta is very small.

In addition, the release patterns between different placentas have an average coefficient of variation of only 25%, 21%, 13%, 16%, and 25%, for PGE, PGF, PGFM, 6-keto-$PGF_{1\alpha}$ and $TxB_2$, respectively, over the perifusion period.

FIG. 1 illustrates the average normalized release patterns (mean±SEM) for these prostanoids from the control chambers of seven different placentas over the perifusion period. In the case of PGE, PGF and 6-keto-$PGF_{1\alpha}$ the rate of release increased significantly (from the fourth to the sixth hour for PGE, from the fourth to the 12th hour normalized releases of PGFM and $TxB_2$ were relatively constant throughout this perifusion period. As can be seen in FIG. 1, the greatest variance is seen in the later hours of the perifusion with relatively small variance between placentas in the earlier perifusion hours, using the fourth-hour normalized data.

TABLE 1

The basal release (mean ± SEM) of PGE, PGF, PGFM, 6-keto-$PGF_{1\alpha}$ and $TxB_2$ expressed as pg per mg wet weight of tissue from seven term placentas during 12 hours of perifusion

| | PGE | | PGF | | PGFM | | 6-keto-$PGF_{1\alpha}$ | | $TxB_2$ | |
|---|---|---|---|---|---|---|---|---|---|---|
| HOUR | (pg/) | mean ± SEM | (pg/) | mean ± SEM | (pg/) | mean ± SEM | (pg/) | mean ± SEM | (pg/) | mean ± SEM |
| 3 | 1043 | 260 | 949 | 141 | 2751 | 254 | 254 | 33 | 6017 | 1284 |
| 4 | 1200 | 285 | 1198 | 165 | 2876 | 242 | 242 | 36 | 4944 | 920 |
| 5 | 1391 | 258 | 1331 | 161 | 2581 | 270 | 254 | 40 | 4348 | 696 |
| 6 | 1704 | 364 | 1534 | 176 | 2808 | 259 | 264 | 34 | 4195 | 592 |
| 8 | 1958 | 301 | 1787 | 233 | 2508 | 282 | 300 | 50 | 4234 | 596 |
| 10 | 2266 | 235 | 1930 | 253 | 2209 | 190 | 286 | 39 | 4328 | 720 |
| 12 | 3181 | 434 | 2288 | 292 | 2428 | 296 | 383 | 66 | 4474 | 599 |

Statistical Analysis

The prostanoid release for a given chamber was expressed as the increase over the fourth-hour prostanoid release for that chamber. Because there may be differences in the amounts of blood vessels and connective tissue among placental explants, the release expressed per unit weight results in high variance between chambers. On the other hand, it was observed that expressing each chamber's response in relation to its initial release resulted in a very low variance between replicate chambers. Thus, the release of each chamber was related to its functional competence at the time of treatment rather than its mass.

The mean release for replicate chambers from a given placenta for each particular prostanoid in the presence of arachidonic acid or each of the various enzyme inhibitors was calculated and then the mean data for each of the three different placentas was averaged at each time point. Thus, each placenta was weighted equally in the statistical analyses. Two-way analysis of variance of the average response for each prostanoid for each dose of arachidonic acid or each enzyme inhibitor studied, at each time point, was performed. The normalized data were tested for homogeneity using Cohrna's Q test, and no significant deviation was found. Thus, for each prostanoid and each treatment, where there was a significant main effect or interaction, Dunnett's comparison test was applied to determine the point(s) of significant difference as compared to the control. $P<0.05$ was considered to be statistically significant.

Placental Prostanoid Release in the Presence of Enzyme Inhibitors

Figure 2:
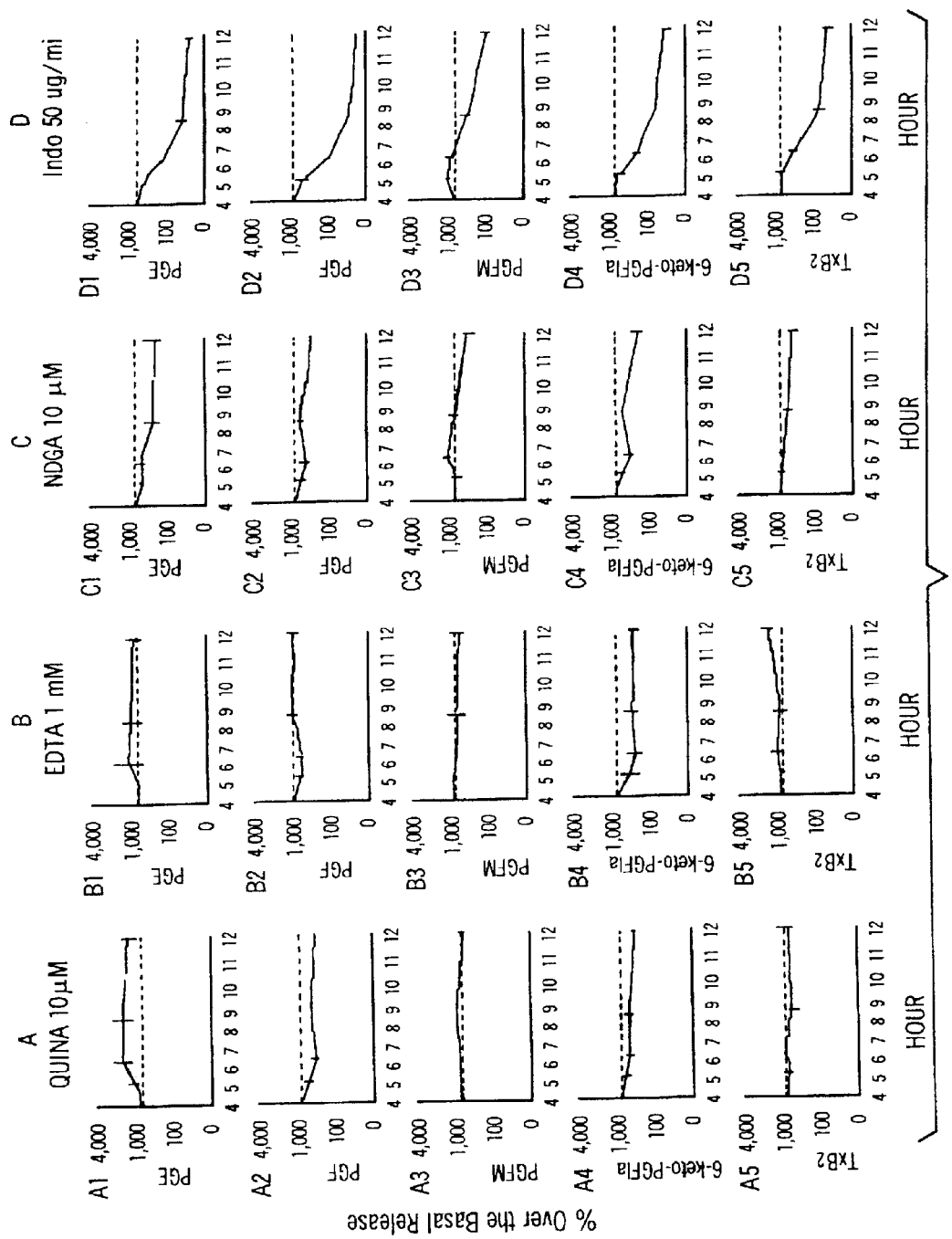
FIG. 2. Effect of eiconasoid enzyme inhibitors on percent release over the control (mean±SEM) of PGE (2A1, 2B1, 2C1, 2D1), PGF (2A2, 2B2, 2C2, 2D2), PGFM (2A3, 2B3, 2C3, 2D3), 6-keto-$PGF_{1\alpha}$ (2A4, 2B4, 2C4, 2D5) and $TxB_2$ (2A5, 2B5, 2C5, 2D5) from human term placenta.

FIG. 2 illustrates the percent response over the control release for each hormone for each enzyme inhibitor studied. Significantly different responses for each prostanoid, comparing the various treatment over time to the controls using two-way analysis of variance, were noted. Points of significant difference were determined, using the mean normalized response of the three different placentas for each prostanoid studied.

The addition of 10 $\mu$M of quinacrine to the perifusion medium had no significant effect on the release of PGE, PGFM, 6-keto-PGF$_1$ or TxB$_2$ from term placental explants (FIG. 2, panels A1–5). For PGF, there was a significant inhibition of its release during the first hour of quinacrine exposure. Thereafter, the PGF release remained less than controls, but this reduction was not significant.

The addition of EDTA (FIG. 2, panels B1–B5) or NDGA (FIG. 2 panels C1–C5) resulted in a significant inhibition of 6-keto-PGF$_{1\alpha}$. The inhibition was significant within the first hour of tissue exposure and was sustained throughout the perifusion period.

The addition of indomethacin (50 $\mu$g/ml) (FIG. 2, panels D1–D5) to the perifusion medium resulted in a rapid inhibition of PGE, PGF, 6-keto-PGF$_{1\alpha}$ and TxB$_2$ release from these placental explants, i.e., 33.5, 22.1, 41.3 and 42.3% of control, respectively, at three hours post-exposure. Continued perifusion with indomethacin inhibited these prostanoid releases to 24.0%, 9.6%, 26.3%, and 30.5% of the control, respectively, yet detectable levels were still observed.

Interestingly, the PGFM release from these placental explants was not inhibited by indomethacin even after three hours of exposure. However, after seven hours of perifusion, indomethacin inhibited PGFM release to 51.8% of the release from the control placental explant cultures.

Quinacrine had little if any significant effect on the release of these prostanoids. Arachidonate may therefore be liberated by phospholipase A$_2$ and may not be rate-limiting in the human term placenta for these prostanoid releases.

Similarly, Ca$^{++}$ chelator which inhibits phospholipase C activity, also did not reduce PGE, PGFM or TxB$_2$ production. The lack of effect of EDTA in these studies may be due to changes in extra-cellular Ca$^{++}$ that did not influence the intra-cellular Ca$^{++}$. However, previous studies by Olson et al. (1983a) have observed an inhibitory action of low extra-cellular Ca$^{++}$ on anion prostanoid release. A significant inhibition of the already low release of 6-keto-PGF$_{1\alpha}$ was observed in the present studies. Thus, the synthesis of PGI$_2$ by prostacyclin synthetase should be Ca$^{++}$-dependent, and the low extra-cellular Ca$^{++}$ milieu should have been translated intra-cellularly. The present data may suggest that increasing Ca$^{++}$ may stimulate prostacyclin release and may also be a means of regulating prostacyclin production.

The addition of NDGA to the medium which inhibited PGE as well as 6-keto-PGF$_{1\alpha}$ (FIG. 2, panels C1–C5) may indicate a regulation at the level of endoperoxide isomerase and prostacyclin synthetase. Previous studies in the hypothalamus (Negro-Vilar et al., 1986) observed no inhibition of PGE in the presence of NDGA. They also noted an increase in GnRH release. The present inventors have demonstrated that GnRH may inhibit prostanoid release from human term placental tissue; thus, the actions of NDGA observed herein may be effected via chorionic GnRH. NDGA also reduced leukotrines.

The reduction of placental PGE, PGF, 6-keto-PGF$_{1\alpha}$ and TxB$_2$ by indomethacin confirms the activity of the placental cyclooxygenase in these prostanoid releases. Interestingly, a significant inhibition of PGFM release was observed only many hours after incubation with indomethacin, thus indicating that the enzyme(s) metabolizing PGF to PGFM were saturated with substrate in the term placenta and only after reduction of PGF production and/or induction of metabolizing enzyme(s), was PGFM release significantly reduced. Observation of the basal release of PGF and PGFM also supports this finding. PGF increases nearly three fold from the fourth to the twelfth hour of perifusion, yet PGFM is constant. This again indicates that the placental enzyme(s) metabolizing PGF to PGFM should be saturated, such that further PGFM release could not occur. These findings differ from previous predictions based on demonstration of the very high activity of metabolizing enzyme in the placenta and the significant metabolism of PGE (Myatt, 1990). However, the activity of PGDH for PGF is one-sixth that for PGE (Jarabak, 1972). Thus, PGF metabolism may be saturated, whereas PGE is not. This may be of physiologic significance, as an increase in cyclooxygenase activity would then lead to an increase in PGF without an increase in PGE.

A comparison of the relative ratio of prostanoid release as reported in the present disclosure demonstrates TxB$_2$ to be produced in the highest amounts. In the system employed in the present studies, the relative release of PGF to its metabolite was greater than that observed by Mitchell et al. (1978c) or Olson et al. (1983c). On the other hand, production of 6-keto-PGF$_{1\alpha}$ was less, probably due to the use of 95% air in the present system rather than 95% O$_2$ which is known to reduce PGI$_2$ production (Ekblad et al., 1987). Because the present studies sought to emulate a physiologic system, 95% air:5% CO$_2$ was employed in the study in vitro system. This aeration resulted in an O$_2$ partial pressure of 100–150 mm Hg, which is a physiologic level in the human term placenta.

Of interest is the striking increase in the basal release for PGE, PGF and 6-keto-PGF$_{1\alpha}$ during the fourth to the twelfth hours using this culture system (see Table 1).

It has been suggested previously that high TxB$_2$ release reflects blood contamination of the tissue (Myatt, 1990). However, in the present studies, the tissue was washed for hours and the initially very high TxB$_2$ release declined over the first three to four hours, persisted at high levels, and then increased again by the 12th hour of perifusion. Thus, the release of TxB$_2$ observed herein from the fifth hour on is indeed due to trophoblastic function.

These studies demonstrate the high biosynthetic competence of the human placenta for prostanoid production. These studies provide a reference for mean production because human placental explants were used. Based on the data provided in the present study a term size placental tissue is estimated to produce greater than 4,000 ng/hour of these five prostanoids alone. The function of the placenta is hypothesized to be both endocrine and paracrine due to its vasculature and its intra-uterine position. These factors, together with the teachings of the present disclosure, are used in the definition of the herein disclosed methods to regulate chorionic prostanoid production to affect uterine, fetal and intra-uterine function in the management of labor.

EXAMPLE 3

Effect of Arachidonic Acid on Placental Prostanoid Release

Prostaglandins and prostanoids, including prostacyclin, thromboxane A$_2$, and the leukotrines, are formed from certain polyunsaturated fatty acids, principally arachidonic acid. The present example demonstrates that prostanoid production by the human placenta is not limited by arachidonic acid availability.

The effect of exogenous arachidonic acid on basal prostanoid release was studied by perifusing placental tissue from the beginning of the fifth hour of the perifusion, with Medium 199 containing arachidonic acid (0.2, 1.0 or 10 µg/ml). Arachidonic acid was dissolved in ethanol such that 0.02 ml ethanol per 100 ml of Medium 199 was needed to obtain these concentrations, and the resulting ethanol concentration was 0.02%. The control medium was also made to be 0.02% ethanol for valid comparison of the arachidonic acid parameter only. Four replicated chambers were perifused with control medium and each of the experimental arachidonic acid media. This experimental design was repeated using placental tissues from three different patients.

Prostanoid Recovery and Stability

Samples were stored at −20° C. until assayed for PGE, PGF, PGFM, $TxB_2$ and 6-keto-$PGF_{1\alpha}$. Recovery and stability of these prostanoids in the perifusion system used in the present studies and during storage was assessed by spiking the medium with prostanoids and perifusing it through empty chambers and collecting samples as described above. In addition, samples were frozen and thawed repeatedly and re-assayed. Prostanoid recovery and stability was nearly 100%.

Materials

Medium 199 (×2) with Earles' Modified Salts, bicarbonate and L-glutamine without phenol red was purchased from Gibco Laboratories (Chargin Falls, Ohio). Penicillin, streptomycin and bovine serum albumin were obtained from Sigma Chemicals (St. Louis, Mo.). Quinacrine, NDGA, EDTA and indomethacin were also purchased from Sigma Chemicals. Arachidonic acid was obtained from Sigma Chemicals by overnight mail and used within one week of receipt. IGF-I was purchased from Chemicon International, Inc. (Terecula, Calif.).

Placental Perifusion

A perifusion system was employed to investigate the release of prostaglandin E (PGE), prostaglandin F (PGF), PGFM and the stable metabolites of thromboxane $A_2$ ($TxB_2$) and $PGI_2$, i.e., thromboxane $B_2$ ($TxB_2$) and 6-keto-prostaglandin $F_{1\alpha}$ (6-keto-$PGF_{1\alpha}$) from human term placentas. The effect of increased availability of arachidonic acid and inhibitors of arachidonic acid metabolism, such as quinacrine, and of enzyme inhibitors, such as EDTA, nordihydroguaiaretic acid (NDGA) and indomethacin, was compared to basal placental prostanoid release. These studies provide new data relating to rate-limiting steps in the basal release of prostanoids from the human term placenta. Human placental tissues were prepared and placental perifusion conducted as described in Example 2.

Briefly, term placenta were obtained and placed on ice immediately after vaginal delivery from patients having spontaneous labor and delivery without any known obstetrical or medical complications. Tissues were obtained in accordance with a protocol approved by the Institutional Review Board. Within 30 minutes, the placental tissues were dissected of decidua, chorionic plates and large fetal vessels on ice. The placental tissues were cut into small fragments (approximately 25 pieces having a total weight of approximately 1 g), rinsed free of blood by repeated washing with ice cold normal saline until clear in color, and the tissue fragments placed in a 3-ml tissue chamber, placed in a 37° C. water bath. Twenty replicate chambers were prepared and each perifused with Medium 199 containing 0.05% BSA, 100 U penicillin and 100 µg streptomycin per ml at a rate of 1 ml per hour for 12 hours. This medium is hereafter referred to as Medium 199. The influx medium was aerated with 95% air and 5% $CO_2$ throughout the perifusion. Perifusion was performed for two hours prior to initiation of sample collection. In this fashion, all tissues were thoroughly washed and equilibrated. Samples were collected hourly, beginning at the start of the third hour, into 12×75 mm glass tubes containing 0.1 ml indomethacin and 1100 µg/ml dimethyl sulfoxide [DMSO]. It took approximately one hour for the input medium to pass through the perifusion tubing and chamber and to be collected in the sample tube, thus the dead volume of the system was approximately 1 ml. Collection of the effluent of the 20 chambers was done simultaneously, using an ISCO fraction collector Retriever III adapted with a 20-tube rack and manifold.

Statistical Analysis

The prostanoid release for a given chamber was expressed as the increase over the fourth-hour prostanoid release for that chamber. Because there may be differences in the amounts of blood vessels and connective tissue among placental explants, the release expressed per unit weight results in high variance between chambers. On the other hand, it was observed that expressing each chamber's response in relation to its initial release resulted in a very low variance between replicate chambers. Thus, the release of each chamber was related to its functional competence at the time of treatment rather than its mass.

The mean release for replicate chambers from a given placenta for each particular prostanoid in the presence of arachidonic acid or each of the various enzyme inhibitors was calculated and then the mean data for each of the three different placentas was averaged at each time point. Thus, each placenta was weighted equally in the statistical analyses. Two-way analysis of variance of the average response for each prostanoid for each dose of arachidonic acid or each enzyme inhibitor studied, at each time point, was performed. The normalized data were tested for homogeneity using Cohrna's Q test, and no significant deviation was found. Thus, for each prostanoid and each treatment, where there was a significant main effect or interaction, Dunnett's comparison test was applied to determine the point(s) of significant difference as compared to the control. $P<0.05$ was considered to be statistically significant.

The present findings that increasing the availability of free arachidonic acid to 1 µg/ml did not result in an increase of any of the five prostanoids studied, suggests that availability of arachidonic acid may not be rate-limiting for the term placenta under these conditions. The present demonstration that this concentration of arachidonic acid is at least five times greater than the endogenous tissue arachidonate provides convincing data that substrate availability was not a limiting factor in the production of these placental prostanoids. In addition, it should be appreciated that the hourly production of these five prostanoids would require less than 5% of the endogenous level of free placental arachidonate. Thus, the present studies support the finding that, in the human placenta, the availability of arachidonate is not the primary rate-limiting step regulating prostanoid production.

In addition, the differing patterns of release among these prostanoids indicate that enzymes beyond the cyclooxygenase are regulating their relative releases. Our finding, that the high concentration of 10 µg/ml of arachidonic acid in the perfusing medium increased only PGE and PGF, again demonstrates differential regulation of these prostanoids. The observation that this increase of PGE and PGF occurred only after two to three hours' incubation with this level of arachidonic acid suggests that induction of increased enzyme activity may have occurred before the increased PGE and PGF production could be effected.

Arachidonic Acid Content in Perifused Placental Explants

Placental explants were perifused for five hours with Medium 199 as described above; each was immediately removed from its perifusion chamber, then placed in phosphate buffer (1 ml, 0.05M, pH 7.6) with 0.1 ml indomethacin (1100 µg/ml DMSO). The tissue was then homogenized and extracted three times with ethyl acetate (3.1 ml). The organic layers were combined and dried under nitrogen. The dried extract was resuspended in chloroform:methanol (20 ml, 2:1) and 1 ml of water. The extract was then divided into a 1 ml aliquot which was spiked with 5 µg arachidonic acid and a 20 ml aliquot which was not spiked. Each aliquot was filtered using a Millipore filter (HVLP 0.45 microns) and the filter rinsed twice with 5 ml of chloroform:methanol (2:1). The extract was emulsified with water (6:1) and centrifuged to separate the aqueous and organic phases. The aqueous phase was discarded and the organic phase dried under nitrogen. A standard arachidonic acid sample (5 µg) was also extracted in a similar fashion. The arachidonic acid in the extract and the spiked extract and the standard sample were quantitated using HPLC (Milton-Roy CM 4000 and spectromonitor 3100). The samples were resuspended in ethanol and chromatographed using a C-18 column (Ultrasphere-ODS, 10×0.5 cm). An isocratic mobile phase of 68% acetonitrile in water was used. Elution was monitored at an optical density at 195 nm and recorded using the Milton-Roy integrator Model C4100. The primary peak of arachidonic acid eluted at approximately 19.9 min and was quantitated by comparison of the height and area under the curve to varying doses of the 5 µg arachidonic acid sample.

Addition of varying doses of arachidonic acid (0.2–10 µg/ml) had no significant effect on PGFM, $TxB_2$ or 6-keto-$PGF_{1\alpha}$, although the endogenous arachidonate was similar to or much less than the doses studied. Only at the 10 µg/ml dose was a delayed increase of PGE and PGF observed.

Figure 3:
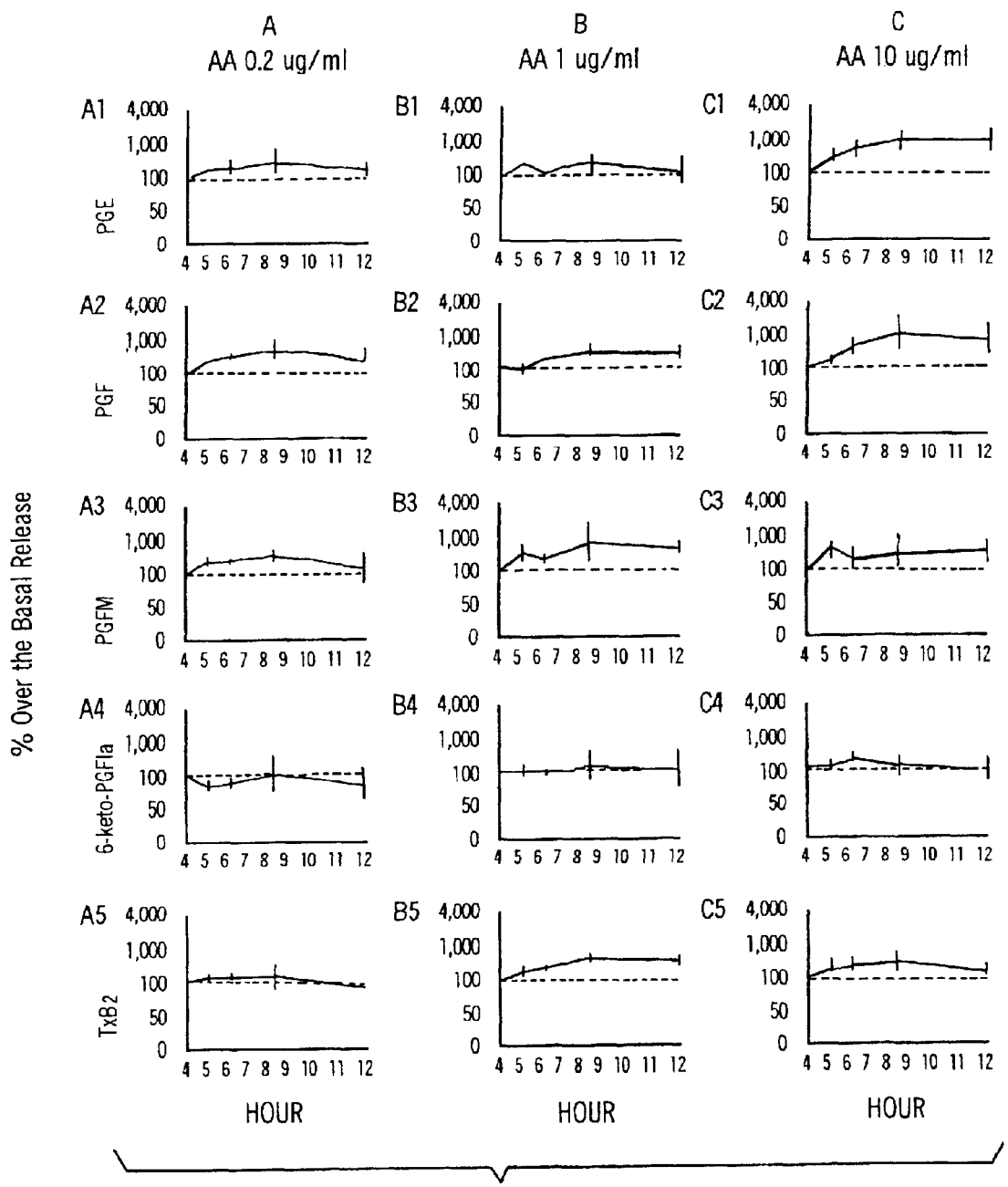
FIG. 3. Effect of arachidonic acid (0.2, 1.0 or 10 μg/ml) on the release of PGE (3A1, 3B1, 3C1), PGF (3A2, 3B2, 3C2), PgFM (3A3, 3B3, 3C3), 6-keto-$PGF_{1\alpha}$ (3A4, 3B4, 3C4) or $TxB_2$ (3A5, 3B5, 3C5) from human term placenta expressed as percent over control (mean±SEM).

Prostanoid Recovery and Placental Prostanoid Release in the Presence of Arachidonic Acid FIG. 3 illustrates the mean percent change over the control release for each hormone at each dose of arachidonic acid studied for the three placentas (%±SEM). Significantly different responses for each prostanoid, comparing the various doses of arachidonic acid over time to controls, using two-way analysis of variance, were noted. Points of significant difference were determined, using the mean normalized response of the three different placentas for each prostanoid studied.

The inclusion of exogenous arachidonic acid in the perifusing medium at 0.2 (FIG. 3, panels A1–A5) or 1.0 µg/ml (FIG. 3, panels B1–B5) had no significant effect on prostanoid production using this perifusion system. In some instances, increased productions over the control (as indicated by the 100% dashed line) was observed, yet significance was not attained. However, the addition of 10 µg/ml of arachidonic acid did induce a significant increase in PGE and PGF release within three hours of exposure of the placental tissue to this precursor (FIG. 3, panels C1–C5). Continued perifusion with arachidonic acid resulted in continuation of the significantly increased release of these two prostanoids.

Endogenous free arachidonate in the placental explants after five hours of perifusion, i.e., the time when tissue was first exposed to exogenous arachidonic acid, was found to be ≦200 ng/gram of tissue. Approximately one gram of tissue was used in each chamber. Thus, the doses of exogenous arachidonic acid utilized in these studies were at least 50 fold, 5 fold, or equimolar to the endogenous free arachidonate in the placental explants.

These data demonstrate that prostanoid production from the human term placenta is not limited by arachidonic acid availability, and that enzyme inhibitors of extra-cellular chelating agent have little immediate effect on prostanoid release, with the exception of $PGI_2$. However, increasing arachidonic acid levels to very high concentrations may activate endoperoxide isomerase activity, resulting in increased PGE and PGF release. In addition, the production of PGFM appears to be saturated by the endogenous production of PGF; therefore, the PGF produced cannot be totally metabolized by the placenta.

EXAMPLE 4

Estrogen and Estrogen/Progesteronr on Production of 6-KETO-$PGF_{1\alpha}$, PGE and PGF by Placenta The present example demonstrates that estradiol or a combination of estradiol and progesterone affects 6-keto-$PGF_{1\alpha}$, PGE and PGF release from perifused human term placenta, yet does not affect the release of $TxB_2$, PGFM or hCG. The basal release of prostaglandin E (PGE), prostaglandin F (PGF), thromboxane ($TxB_2$) and 6-keto-prostaglandin $F_{1\alpha}$ (6-keto-$PGF_{1\alpha}$) increased from the fifth hour in culture, while the release of 13, 14-dihydro-15-keto-$PGF_{2\alpha}$ (PGFM) remained constant and hCG release decreased. The dose-related effect of estradiol (20–2,000 ng/ml) in the perifusing medium effected no change in the release of $TxB_2$, PGFM or hCG. Only the release of 6-keto-$PGF_{1\alpha}$ was significantly increased at 60–120 min after exposure to 200 ng/ml of estradiol. The cumulative release of 6-keto-$PGF_{1\alpha}$ to estradiol was biphasic with inhibition at the 20 ng/ml dose and stimulation at 200 ng/ml. The concomitant addition of progesterone (2,000 ng/ml) with estradiol (200 ng/ml) significantly inhibited the stimulatory action of estradiol.

The release of PGE and PGF was increasingly reduced with increasing does of estradiol, but at no particular time point was the inhibition significant. However, a significant dose-related inhibition of PGE release was found when the cumulative release over the four hours of estradiol exposure was compared to the untreated controls. The addition of progesterone with estradiol (2,000 and 200 ng/ml, respectively) reversed the inhibition of PGE by estradiol alone.

These data demonstrate that physiologic levels of estradiol affect 6-keto-$PGF_{1\alpha}$, PGE and PGF release from the human term placenta, but do not significantly alter production of $TxB_2$, PGFM or hCG under these conditions. In these studies, the dose-related action of estradiol on PGE, PGF, PGFM, $TxB_2$, 6-keto-$PGF_{1\alpha}$ and hCG production is demonstrated, using a perifusion system for human placental explants. In addition, the effect of progesterone in combination with estradiol on the release of these placental prostanoids is provided.

Materials

Medium 199 (×2) with Earles' Modified Salts, bicarbonate and L-glutamine without phenol red was purchased from Gibco (Chargin Falls, Ohio). Penicillin, streptomycin, bovine serum albumin estradiol, progesterone and indomethacin were obtained from Sigma Chemicals (St. Louis, Mo.).

Placental Perifusion

Term placentas were obtained and processed as described herein. The placental tissues were cut into small fragments (approximately 25 pieces having a total weight of approximately 1 g), rinsed free of blood by repeated washing with ice-cold normal saline until clear in color, and the tissue fragments placed in a 3 ml tissue chamber, placed in a 37° C. water bath. Twenty replicate chambers were prepared and each perifused with Medium 199 containing 0.05% BSA, 100 U penicillin and 100 μg streptomycin per ml at a rate of 6 ml/hour for nine hours. This medium is hereafter referred to as Medium 199. The influx medium was aerated with 95% air and 5% $CO_2$ throughout the perifusion. Perifusion was performed for four and one-half hours prior to initiation of sample collection. In this fashion, all tissues were thoroughly washed and equilibrated. Sample collection was every 15 minutes, beginning at four and one-half hours, into 12×75 mm glass tubes containing 0.1 ml indomethacin (1,100 μg/ml dimethyl sulfoxide [DMSO]). Collection of the effluent of the 20 chambers was done simultaneously, using an ISCO fraction collector Retriever III adapted with a manifold and a rack having 20 tubes.

Effect of Estradiol or Estradiol and Progesterone on Placental Prostanoid Release To study the effect of estradiol or estradiol and progesterone on basal prostanoid release, ten minutes prior to the beginning of the fifth hour of the perifusion, Medium 199 in the experimental chambers was changed to Medium 199 containing estradiol (20, 200, 2,000 ng/ml) or to estradiol and progesterone (200 and 2,000 ng/ml, respectively). These concentrations were chosen to simulate concentrations in intrauterine tissues at term. It took ten minutes for the input medium to pass through the perifusion tubing and chamber and to be collected in the sample tube. Four replicated chambers were perifused with each experimental medium, while, in another four replicated chambers, the perifusion was continued with the control Medium 199. This experimental design was repeated using placental tissues from three different patients who had had normal pregnancies.

Prostanoid Recovery and Stability

Samples were stored at −20° C. until assayed for PGE, PGF, PGFM, $TxB_2$, 6-keto-$PGF_{1\alpha}$ or hCH. Recovery and stability of these prostanoids in this perifusion system and during storage were assessed by spiking the medium with prostanoids, perifusing it through empty chambers and collecting samples as described above. In addition, samples were frozen and thawed repeatedly and re-assayed. Prostanoid recovery and stability were nearly 100%. Thus, no data correction for procedural loss was done.

Radioimmunoassays

Radioimmunoassays were performed in a fashion similar to what has been previously described herein at Example 1. Samples collected at −30, 0, 30, 90, 120, 150, 180 and 240 minutes were chosen for assay and for data analyses. All the samples from a given perifusion (placenta) were quantitated in the same assay.

Statistical Analysis

Hormonal values for a given chamber were normalized to the fifth hour prostanoid or hCH release for that chamber and expressed as a percent release over the fifth-hour release. Because of differences in the amount of blood vessels and connective tissue among placental explants, the release expressed per unit weight resulted in a higher variance between chambers. On the other hand, expressing each chamber's response in relation to its fifth-hour release resulted in a very low variance between chambers. Thus, the release of each chamber was related to its functional competence at the time of treatment rather than to it mass.

The mean release for replicate chambers from a given placenta for each particular hormone in the presence of each dose of estradiol or estradiol and progesterone at each time point was calculated. Similar calculations were done for the control chambers. The mean data for controls and each treatment for the three different placentas were subject to statistical analyses. Thus, the response for each placenta was weighed equally. For each hormone studied, the normalized data from each placenta were tested for homogeneity using Bartlett's test and, if significant deviation was found, the data were log-transformed prior to statistical analysis. Two-way analysis of variance was used to determine if there was a significant main effect or interaction. If so, one-way analysis of variance and the Student-Newman-Keul test were used to determine the significantly different points as compared to the control. A value of $p<0.05$ was considered to be statistically significant.

In addition, the cumulative release for each hormone from each placenta for each treatment was calculated, using the sum of the normalized release from 30 to 240 minutes. One-way analysis of variance was used to test for statistical effects of treatment. The points of significant variation were determined using the Student-Newman-Keuls test. Linear line regression analysis was used to determine the significance of the dose-response effect of estradiol.

Figure 4:
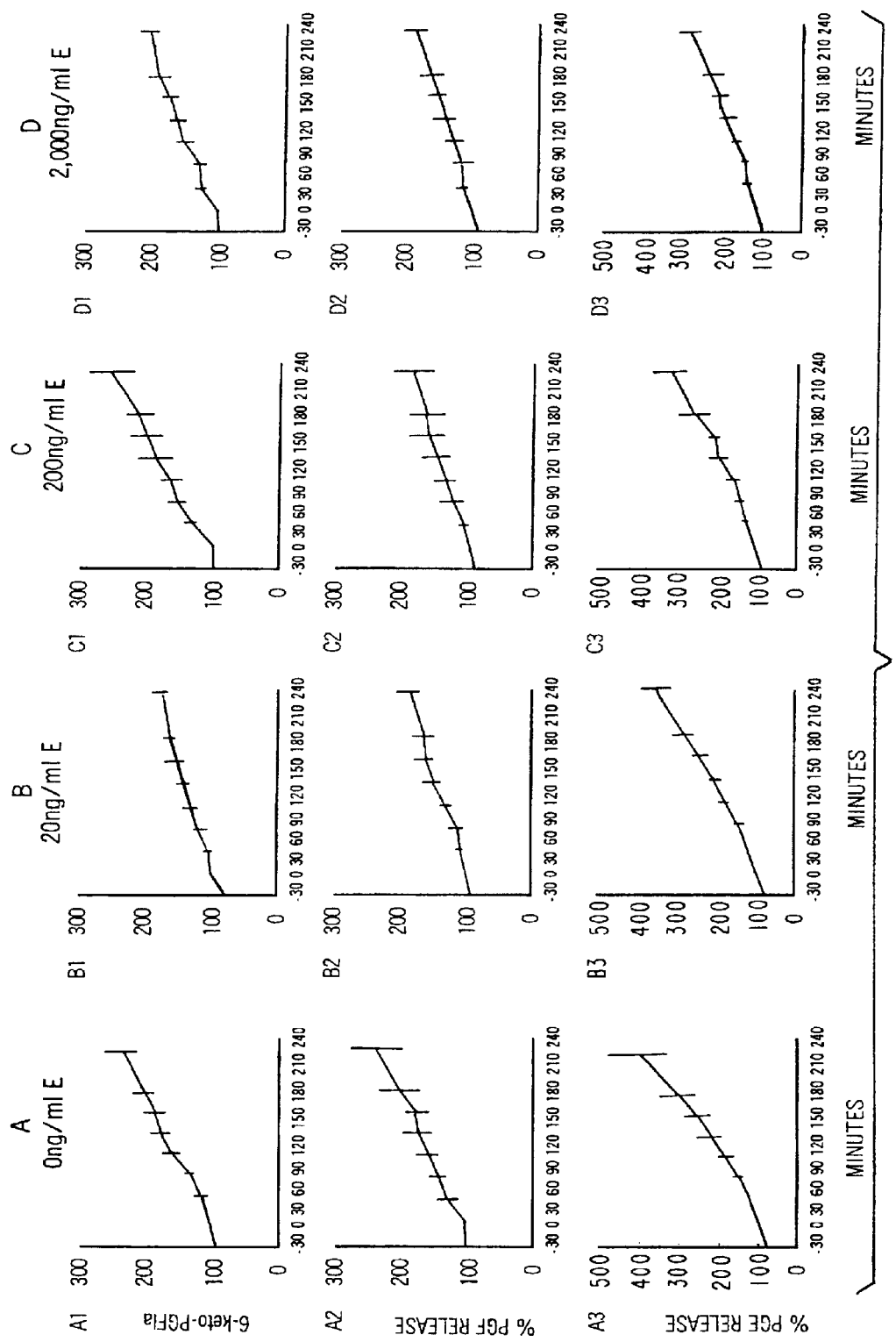
FIG. 4. The effect of estradiol (control=0 ng/ml; 20 ng/ml; 200 ng/ml; 2,000 ng/ml) on the fifth-hour normalized release of 6-keto-$PGF_{1\alpha}$, PGF and PGE is shown. Points of significant difference are indicated (*p<0.02, **p<0.05).

Results The basal release (mean±sem) of 6-keto-$PGF_{1\alpha}$, PGF, PGE, $TxB_2$, PGFM and hCG was 99±37, 562±207, 749±313, 1,680±588, 1,602±639 and 6±2, respectively. When the hormonal release of 6-keto-$PGF_{1\alpha}$, PGF, PGE, and $TxB_2$ was normalized to the fifth-hour release, each increased from the fifth to the ninth hour in culture to 234%, 228%, 417% and 138%, respectively. However, the release of PGFM was constant during the 4.5 experimental hours of perifusion, whereas the release of hCG declined to 59% of the zero time release during the following hours of perifusion. The release pattern between these three placentas had an average coefficient of variation of only 12.9%, 20.3%, 17.3%, 12.2%, 10.5% and 6.6% for 6-keto-$PGF_{1\alpha}$, PGF, PGE, $TxB_2$, PGFM and hCG, respectively, over the perifusion period. FIG. 4 illustrates the normalized release patterns (mean±sem) for 6-keto-$PGF_{1\alpha}$ (FIG. 4, panels 1, B1, C1, D1), PGF (FIG. 4, panels A2, B2, C2, D2) and PGE (FIG. 4, panels A3, B3, C3, D3) throughout the perifusion period.

Figure 5:
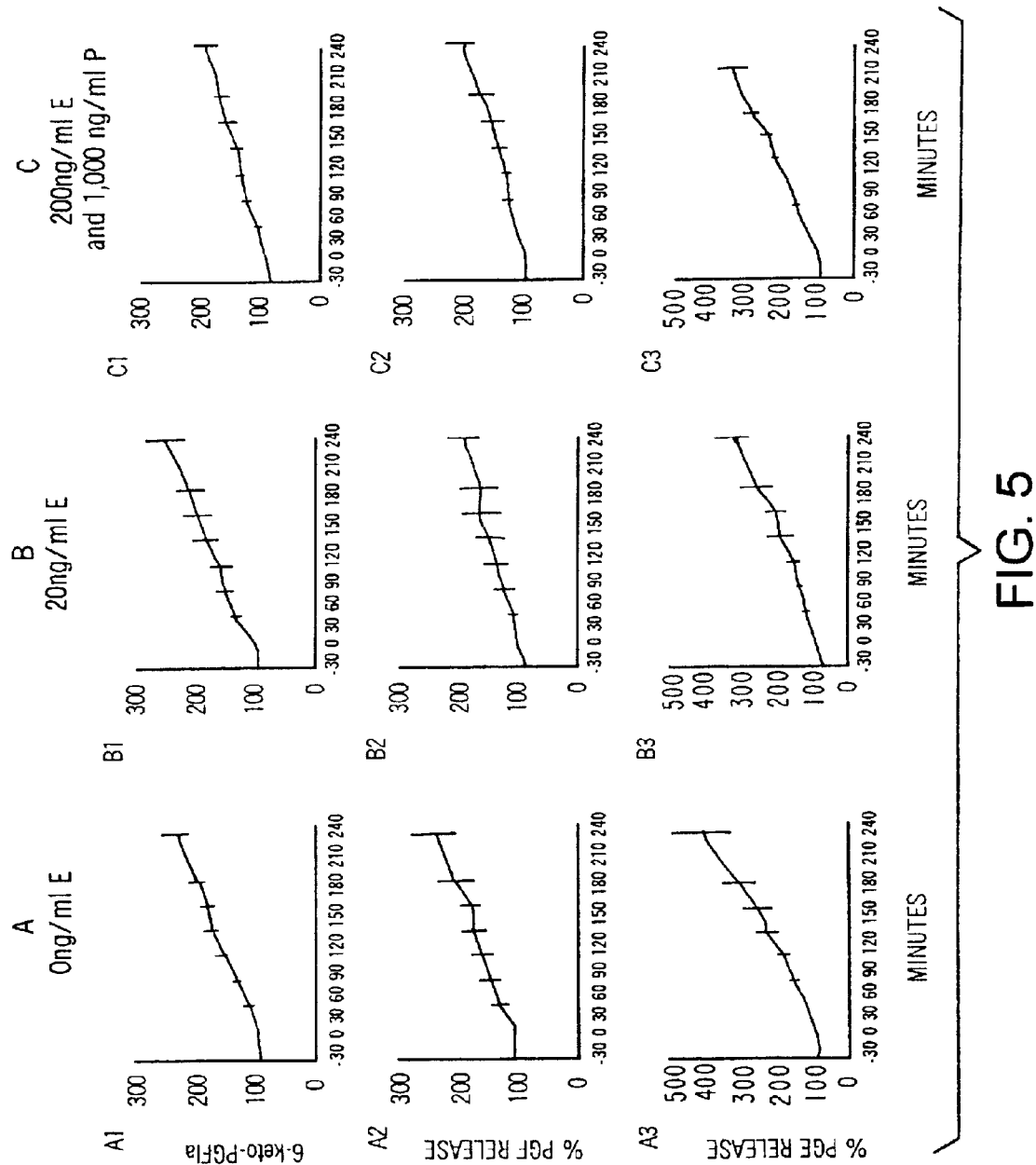
FIG. 5. The effect of estradiol and progesterone (200 and 2,000 ng/ml, respectively), as compared to estradiol alone (200 ng/ml) or no estradiol or progesterone (control) for the fifth-hour normalized release of 6-keto-$PGF_{1\alpha}$, PGF and PGE is shown. Points of significant difference are indicated (*p<0.02, **p<0.05).
Figure 6:
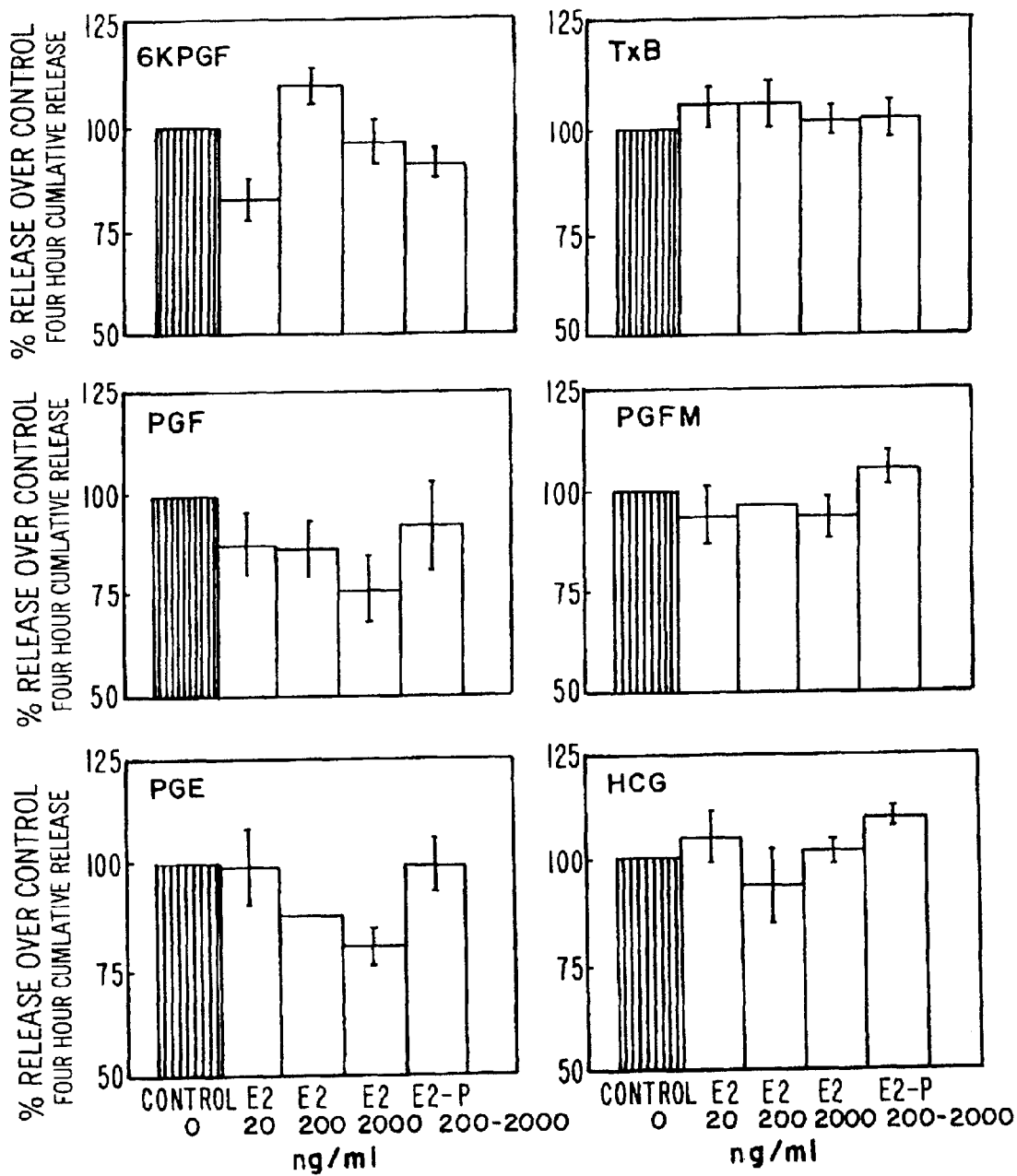
FIG. 6. The cumulative release of 6-keto-$PGF_{1\alpha}$, PGF, PGE, $TxB_2$, PGFM and hCG, expressed as a percentage of the cumulative release from the controls is illustrated. Points of significant difference are indicated (*p<0.02, **p<0.05). Significant dose-related responses are indicated.

The effect of varying doses of estradiol in the perifusion medium on the release of 6-keto-$PGF_{1\alpha}$, PGF and PGE is also illustrated in FIG. 4. A biphasic action of estradiol on the prostacyclin metabolite was observed. Low doses of estradiol resulted in a reduction of 6-keto-$PGF_{1\alpha}$ release, as compared to the physiological dose of estradiol (200 ng/ml) at 60 minutes ($p<0.04$), whereas a physiologic or higher concentration of estradiol led to a stimulation of 6-keto-$PGF_{1\alpha}$ release at 30 minutes ($p<0.02$). Addition of progesterone (2,000 ng/ml) together with the estradiol (200 ng/ml) blocked the stimulatory action of 200 ng/ml estradiol alone (FIG. 5). The cumulative release of 6-keto-$PGF_{1\alpha}$ over the four hours of perifusion was also inhibited by low doses of progesterone ($p<0.02$) and stimulated by physiologic concentration of estradiol (FIG. 6). This cumulative stimulation of 6-keto-$PGF_{1\alpha}$ was reversed by progesterone.

PGF release was not significantly affected by the addition of estradiol or estradiol and progesterone to the perifusing medium of these placental explants (FIG. 4, panels B2, C2, and FIG. 5, panels B2, C2, (middle graphs), although a trend toward decreasing release with increased estradiol concentration was observed. The cumulative release of PGF (FIG. 6) was inhibited in a dose-related fashion with increasing estradiol concentration ($r=0.609$, $p<0.02$).

The release of PGE from these placental explants was also suppressed by the addition of estradiol (FIG. 4). Although the decrease of PGE release by estradiol was not significant at any given time point, the cumulative release over the four hours of exposure was significantly inhibited ($p<0.05$) (FIG.

6). A dose-related inhibition with increasing estradiol concentration was observed (r=0.738, p<0.005). The concomitant addition of estradiol and progesterone resulted in a reversal of the estradiol effect (FIGS. 5 and 6).

On the other hand, the release of $TxB_2$, PGFM and hCG was not affected by exposure to estradiol or estradiol and progesterone in the does range studied at any given time point studied. Neither was the cumulative release for $TxB_2$, PGFM nor hCG affected by estradiol or estradiol and progesterone (FIG. 5).

In these studies, the action of estradiol or estradiol and progesterone at concentrations lower than, similar to, or higher than intrauterine concentrations in normal term placentas was defined. Estradiol was demonstrated to modulate placental 6-keto-$PGF_{1\alpha}$ production in a biphasic fashion, whereas it inhibits PGE and PGF release in a dose-related fashion. Yet, in the presence of physiological concentration of progesterone, the action of estradiol by itself can be reversed.

In the studies reported herein, no significant changes were observed for PGFM with estradiol alone or in combination with progesterone. The action of progesterone alone was not examined. In prior studies by the present inventor, changes in PGFM release from human term placental explants were not affected, which led to the finding that the enzymatic capacity of the metabolizing enzyme(s) was saturated.

6-keto-$PGF_{1\alpha}$, the metabolite of prostacyclin, is a potent vasodilator, and is thought to play an important role in vasodilation of the placenta. Thus, a stimulation of 6-KETO-Pgf1α release is contemplated by the pressure methods lead to vasodilation, or an inhibition in its production may lead to vasoconstriction. Estradiol at low levels has an inhibitory action on 6-keto-$PGF_{1\alpha}$, whereas physiologic levels stimulate placental 6-keto-$PGF_{1\alpha}$ release. Although other investigators have also observed the stimulatory role of estradiol on 6-keto-$PGF_{1\alpha}$ release, no inhibitory action has been noted. This difference might be related to different culture systems. The present studies were done using explants in serum-free defined media, whereas previous studies utilized a cell culture system in a medium containing 10% horse serum. The stimulatory action of physiological concentrations of estradiol can be overridden by progesterone and may lead to decreased prostacyclin production. Increased placental progesterone production in preeclampsia in the presence of normal estradiol levels has been proposed as a causative factor of the reduced prostacyclin production characteristic of this disease.

Thromboxane $B_2$ ($TxB_2$) concentrations were not affected by estradiol or estradiol and progesterone in the medium. Human chorionic gonadotropin (hCG) release from explants fell dramatically during the study period. Addition of estradiol resulted in small prostanoid changes, but did not alter the spontaneous decline of hCG.

Two other factors that have been shown to affect both prostanoid production and steroid release in the human placenta are GnRH and IGF-I. GnRH is shown in the present studies to inhibit PGE, PGF and $TxB_2$. This response may be due to the increased progesterone and estrogen production that results from GnRH-stimulated hCG release. The inhibition of PGE and PGF observed herein could be consistent with a steroid-mediated mechanism for GnRH action, but no decrease in $TxB_2$ was found. This GnRH action would have to have been effected through a different mechanism.

IGF-I, which inhibits estrogen and stimulates progesterone, is demonstrated to effect an inhibition of PGF and $TxB_2$. However, these studies on the effect of low estradiol, alone or in combination with progesterone, did not result in a similar pattern of inhibited prostanoid release (see Example 6). Thus, factors other than steroids should also be involved in the IGF-I action on placental prostanoid production.

EXAMPLE 5

Dexamethasone Effect on Placental Prostanoid Production

In the present example, fresh placental tissue in a placental explant perifusion system is used to demonstrate the effect of dexamethasone on PGE, PGF, PGFM, $TxB_2$ and 6-keto-$PGF_{1\alpha}$ production. In addition, the effect of GnRH in combination with dexamethasone on human term placental prostanoid release is demonstrated.

Materials and Methods

Medium 199 (×2) with Earles' Modified Salts, bicarbonate and L-glutamine without phenol red was purchased from Gibco (Chagrin Falls, Ohio). Penicillin, streptomycin, bovine serum albumin and Indomethacin were obtained from Sigma Chemicals (St. Louis, Mo.). Placental perifusion was performed essentially as described in Example 3.

Prostanoid Recovery and Stability Prostanoid Radioimmunoassays

Samples were stored at −20° C. until assayed for PGE, PGF, PGFM, Tx $B_2$ or 6-keto-$PGF_{1\alpha}$. Recovery and stability of these prostanoids in this perifusion system and during storage were assessed by spiking the medium with prostanoids and perifusing it through empty chambers and collecting samples as described above. In addition, samples were frozen and thawed repeatedly and re-assayed. Prostanoid recovery and stability were nearly 100%. Thus, no data correction for procedural losses was done. Radioimmunoassays were performed as described in Example 1.

Effect of Dexamethasone and GnRH on Placental Prostanoid Release

The perifusion system described at Examples 2 and 3 was used in the present study. At the end of the fourth hour of the perifusion, Medium 199 in th experimental chambers was changed to Medium 199 containing dexamethasone ($10^{-6}$ M), or to GnRH ($10^{-17}$ M), or to dexamethasone and GnRH ($10^{-8}$ M and $10^{-7}$ M, respectively). It took one hour for the input medium to pass through the perifusion tubing and chamber and to be collected in the sample tube. Four replicated chambers were perifused with each of the three experimental media, while, in another four replicated chambers, the perifusion was continued with the control Medium 199. This experimental design was repeated using placental tissues from three different patients, each of whom had a normal pregnancy.

Statistical Analysis

Hormonal values for a given chamber were normalized to the fifth-hour prostanoid release for that chamber, expressed as a percent release over the fifth-hour release. Because of differences in the amounts of blood vessels and connective tissue among placental explants, the release expressed per unit weight resulted in high variance between chambers. On the other hand, each chamber's response in relation to its fifth-hour release resulted in a very low variance between replicate chambers. Thus, the release of each chamber was related to functional competence at the time of treatment rather than to its mass.

The mean release for replicate chambers from a given placenta for each particular hormone in the presence of GnRH, dexamethasone, or GnRH and dexamethasone at each point was calculated. Similar calculations were done for the control chambers. The mean data for each treatment for the three different placentas were subjected to statistical analyses. Thus, the response for each placenta was weighed equally. Two-way analysis of variance was used to determine if there was significant main effect or interaction. If so, one-way analysis of variance and Student-Newman-Keuls test were used to determine the significantly different points as compared to the control (p<0.05 was considered to be statistically significant).

In addition, the cumulative release for each hormone from each treatment was calculated. One-way analysis of variance was used to test for statistically significant effects of treatment. The points of significant variation were determined using Student-Newman-Keuls' test.

Results

Figure 7:
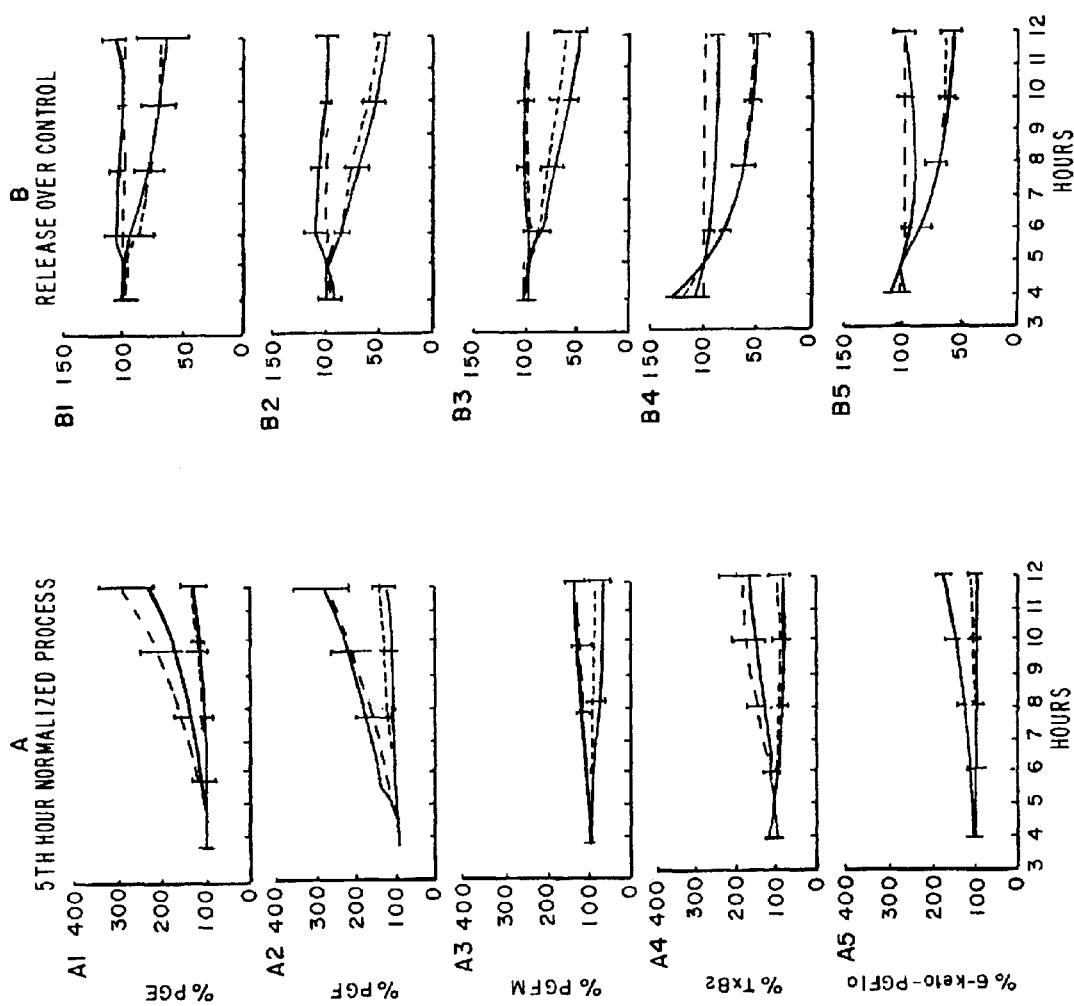
FIG. 7. The release of PGE (7A1, 7B1), PGF (7A2, 7B2), PGFM (7A3, 7B3), $TxB_2$ (7A4, 7B4) and 6-keto-$PGF_{1\alpha}$ (7A5, 7B5) (mean±SEM) from human placental explants, normalized to the fifth-hour release for controls, ●; GnRH ($10^{-7}$ M), ■; dexamethasone ($10^{-8}$ M), ○; GnRH and dexamethasone ($10^{-7}$ M and $10^{-8}$ M), □; (7A); and as normalized to the control release at each time point (7B) is shown. *P<0.05.

The basal release of PGE, PGF, PGFM, $TxB_2$ and 6-keto-$PGF_{1\alpha}$ normalized to the fifth-hour release, increased to 294%, 275%, 190%, 176% and 140%, respectively, by the twelfth hour in culture. The release pattern between these three placentas had an average coefficient of variation of only 19%, 18%, 16%, 27%, and 6% for PGF, PGE, PGFM, $TxB_2$ and 6-keto-$PGF_{1\alpha}$, respectively, over the perifusion period. FIG. 7 (FIGS. 7A1-A-5), dashed lines) illustrates the fifth-hour normalized release pattern (mean±sem) for each of these prostanoids throughout the perifusion period.

Addition of GnRH effected, within the first hour of exposure to GnRH ($10^{-7}$ M), an inhibition of $TxB_2$ that continued throughout the perifusion period (FIGS. 7A4, 7B4). This finding was expected from our prior studies using this concentration of GnRH. Dexamethasone ($10^{-8}$ M) effected a marked inhibition of each of the prostanoids—PGE, PGF, PGFM, $TxB_2$ and 6-keto-$PGF_{1\alpha}$. For PGE, PGF, PGFM, $TxB_2$ and 6-keto-$PGF_{1\alpha}$, the inhibition was already significant within the first hour of incubation with dexamethasone. Only the inhibition of PGFM lagged by one hour. By the seventh hour of incubation with dexamethasone, the suppression of PGE was 68% of its control release, whereas that for PGF was 52%; for PGFM, 65%, for $TxB_2$, 53%; and for 6-keto-$PGF_{1\alpha}$, 63%). FIG. 7 (7B) illustrates the inhibition of release (mean±SEM) for each of these prostanoids as compared to the mean control release at the same time point, and better depicts the marked inhibition of prostanoid release effected by dexamethasone.

Addition of GnRH ($10^{-7}$ M) together with dexamethasone ($10^{-8}$ M) did not alter the action of dexamethasone alone in the case of PGE, PGF, PGFM, $TxB_2$ and 6-keto-$PGF_{1\alpha}$ release. However, PGFM release was significantly inhibited in the presence of both GnRH and dexamethasone by the first hour and, after seven hours of perifusion, was reduced to 50% of its zero time release.

Figure 8:
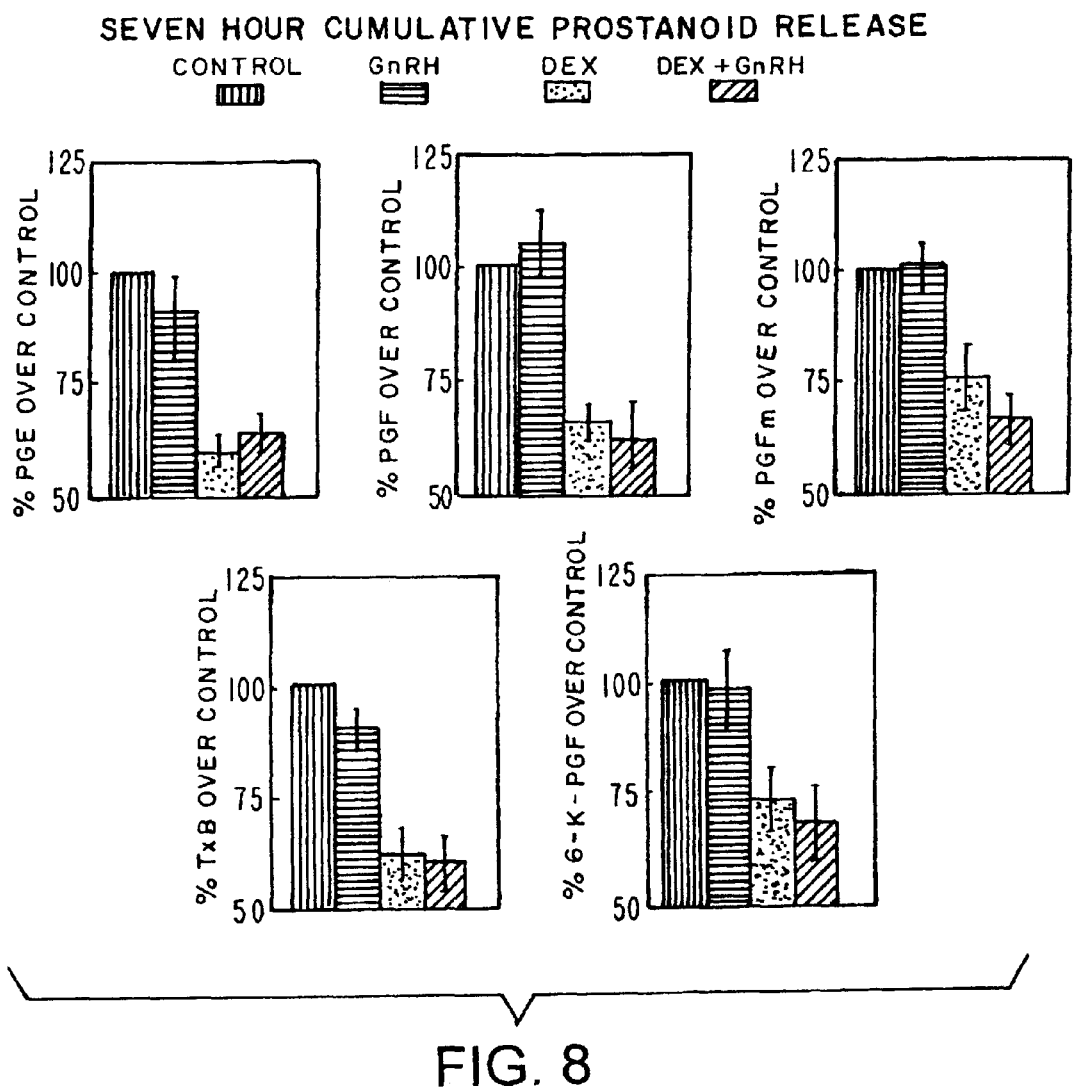
FIG. 8. The cumulative release of PGE, PGF, PGFM, $TxB_2$ and 6-keto-$PGF_{1\alpha}$ (mean±SEM) from human placental explant with or without exposure to GnRH ($10^{-7}$ M), dexamethasone ($10^{-8}$ M) or GnRH and dexamethasone ($10^{-7}$ M and $10^{-8}$ M) as compared to the control is shown p<0.01, *p<0.001.

The cumulative release (mean±SEM) for each of these prostanoids over the seven hours of perifusion for each treatment is shown in FIG. 8. The cumulative release of PGE was significantly inhibited to 66%±4% by dexamethasone or 69%±3% by dexamethasone and GnRH (p<0.0003), whereas PGF was suppressed to 71%±4% or 73%±8%, respectively, by these two treatments (p<0.0008) and further inhibited by the combination of dexamethasone and GnRH to 67%±5%. Although the cumulative PGFM release was less for GnRH and dexamethasone combined, as compared to dexamethasone alone, there was not a statistically significant difference. $TxB_2$ was inhibited by dexamethasone to 62%±6% of the controls and by the combination of dexamethasone and GnRH to 50%±5% (p>0.0009). The inhibition of 6-keto-$PGF_{1\alpha}$ was similar for dexamethasone and dexamethasone and GnRH—73%±7% and 68%±3%, respectively (p<0.0075).

Both PGE and PGF were produced in approximate equimolar ratios, about one half to one third that of $TxB_2$, whereas 6-keto-$PGF_{1\alpha}$ was produced in relatively lesser amounts than the other prostanoids. The release of PGFM at the fifth hour of perifusion was greater (1.5 times) than that of the prostaglandins, yet it did not increase during the perifusion period. However, the basal release for PGE, PGF, PGFM, $TxB_2$ and 6-keto-$PGF_{1\alpha}$ increased during the fifth to the twelfth hour of perifusion. From these data and previous findings Kang et al. (1991) Am. J. Obstet. Gynecol., 165:1771–1776), at least one of the enzymes that metabolizes PGF appears to be saturated under these incubation conditions.

In these studies, dexamethasone ($10^{-8}$ M) is demonstrated to be a potent inhibitor of prostanoid release from the human term placenta. Previous studies have described the effect of glucocorticoids on prostaglandin release from the placenta; however, their effect on PGFM, $TxB_2$ or 6-keto-$PGF_{1\alpha}$ was not reported.

From these data, a role for ACTH and/or glucocorticoids in the modulation of placental cyclo-oxygenase activity may be proposed, because all the prostanoids were inhibited. In addition, the basal increase in prostanoids observed in human term explant cultures may reflect increasing CRH/ACTH or decreasing cortisol inhibition in these term tissues. The finding that dexamethasone suppresses the prostanoids suggests the latter possibility, i.e., that decreasing cortisol inhibition of ACTH may be the operative mechanism in these placental cultures. High dexamethasone may inhibit ACTH release in these tissues, and thus decrease prostanoid production. Other mechanisms to effect the maintenance of basal prostanoid production may also be operative, such as the dexamethasone suppression of lipacortins, which leads to a suppression of prostaglandins.

The observation that GnRH had no further action on prostanoid release indicates that the magnitude of the dexamethasone suppression was so great that the small effect of GnRH could not be appreciated. The hastening of the PGFM inhibition in the presence of GnRH combined with dexamethasone may indicate that this dose of GnRH may also act on the early inhibition of PGF metabolism. The present study clearly indicates that glucocorticoids can be potent regulators of human term placental prostanoid release and that their role in physiological homeostasis of placental paracrine function may be highly significant in the appropriate maintenance of pregnancy, the initiation of labor and normal fetal outcome.

EXAMPLE 6

IGF-I Inhibition of Thromboxane and Prostaglandin $F_{2\alpha}$ Production by Placenta The present example demonstrates the selective inhibition of thromboxane $B_2$ and $PGF_{2\alpha}$ provided by insulin like growth factor treatment of human placental cells. This example also demonstrates the utility of the claimed methods for regulating labor in an animal, such as in farm animals and humans. Using the findings of the present example, insulin like growth factor and specific inhibitors of insulin like growth factor, may be used to inhibit a pre-term onset of labor (administer IGF-I), or to induce labor in a gestational post-term pregnancy (administer an inhibitor of IGF-I or reduce concentrations or activity of IGF-I in vivo).

Materials

Medium 199 (×2) with Earles' Modified Salts, bicarbonate and L-glutamine without phenol red was purchased from Gibco (Chargin Falls, Ohio). Penicillin, streptomycin, bovine serum albumin and indomethacin were obtained from Sigma Chemicals (St. Louis, Mo.). Arachidonic acid was obtained from Sigma Chemicals by overnight mail and used within one week of receipt. IGF-I was purchased from Chemicon (Temecula, Calif.).

Placental Perifusion

Term placentas were obtained and processed as described herein. Seven replicate chambers were prepared and each perifused with Medium 199 containing 0.05% BSA, penicillin (100 U/ml), streptomycin (100 μg/ml), estradiol (200 ng/ml), progesterone (2000 ng/ml), dexamethasone ($10^{-8}$ M), and insulin (100 μU/ml), at a rate of 6 ml/hour for 10.5 hours. Steroids were first dissolved in ethanol at $10^{-4}$M final concentration and taken to final dilution with BSA-containing medium. This medium is hereafter referred to as Medium 199. These concentrations of steroid were chosen because they are known by those in the obstetrical arts to simulate the intrauterine milieu in vivo in humans. The influx medium was aerated with 95% air and 5% $CO_2$ throughout the perifusion. Perifusion at a rate of 6 ml/hr was performed for four hours prior to initiation of sample collection. In this fashion, all tissues were thoroughly washed and equilibrated. Samples were collected every half-hour, beginning at the start of the fourth hour, into 12×) 75 mm glass tubes containing 0.1 ml indomethacin (1100 μg/ml dimethyl sulfoxide [DMSO]). Collection of the effluent of the seven chambers was done simultaneously, using an ISCO fraction collector Retriever III adapted with a rack having seven tubes and a manifold.

To study the effect of IGF-I on basal prostanoid release, ten minutes prior to the beginning of the fifth hour of the perifusion, Medium 199 in the experimental chambers was changed to Medium 199 containing IGF-I ($10^{-8}$ M). This dose of IGF-I was chosen from calculations of the inventor using the Km of the placental receptor for IGF-I. It took ten minutes for the input medium to pass through the perifusion tubing and chamber and to be collected in the sample tube. Three replicated chambers were perifused with experimental medium, whereas, in another four replicated chambers, the perifusion was continued with the control, Medium 199. This experimental design was repeated using placental tissues from three different patients each having a normal pregnancy.

Prostanoid Recovery and Stability; Prostanoid Radioimmunoassays

Prostanoid recovery and stability was determined as described in Example 1. Prostanoid radioimmunoassay was also conducted as described in Example 1.

Statistical Analysis

Hormonal values for a given chamber were normalized to the fifth-hour prostanoid or hCG release for that chamber, expressed as a percent release over the fifth-hour release. Because there may be differences in the amount of blood vessels and connective tissue among placental explants, the release expressed per unit weight results in high variance between chambers. On the other hand, expressing each chamber's response in relation to its fifth-hour release resulted in a very low variance between replicate chambers. Thus, the release of each chamber was related to its functional competence at the time of treatment rather than to its mass. The mean release for replicate chambers from a given placenta for each particular hormone in the presence of IGF-I at each time point was calculated and the mean data for each of the three different placentas were averaged at each time point. Thus, each placenta was weighed equally in the statistical analyses. Similar calculations were done for the controls as for the experimental chambers. For each hormone studied, these average normalized data were tested for homogeneity, using Bartlett's test, and if significant deviation was found, the data were log-transformed prior to statistical analysis. Two-way analysis of variance was used to determine if there was significant main effect or interaction. If so, one-way analysis of variance and Student-Newman-Keuls test were used to determine the significantly different points as compared to the control ($P<0.05$ was considered to be statistically significant).

In addition, the cumulative release for each hormone from each placenta for each treatment was calculated. One-way analysis of variance was used to test for statistical effects of treatment. The points of significant variation were determined using the Student-Newman-Keuls test.

Results

The basal release of prostaglandin E (PGE), prostaglandin F (PGF), thromboxane ($TxB_2$) and 6-keto-prostaglandin $F_{1\alpha}$ (6-keto-$PGF_{1\alpha}$) increased from the fifth hour in culture, while the release of 13, 14-dihydro-15-keto-$PGF_{2\alpha}$ (PGFM) remained constant and hCG release decreased in control cultures. The addition of IGF-I ($10^8$ M) to the perifusing medium effected a significant inhibition of PGF within two and one-half hours of exposure. However, the release of PGE was not altered.

Figure 9:
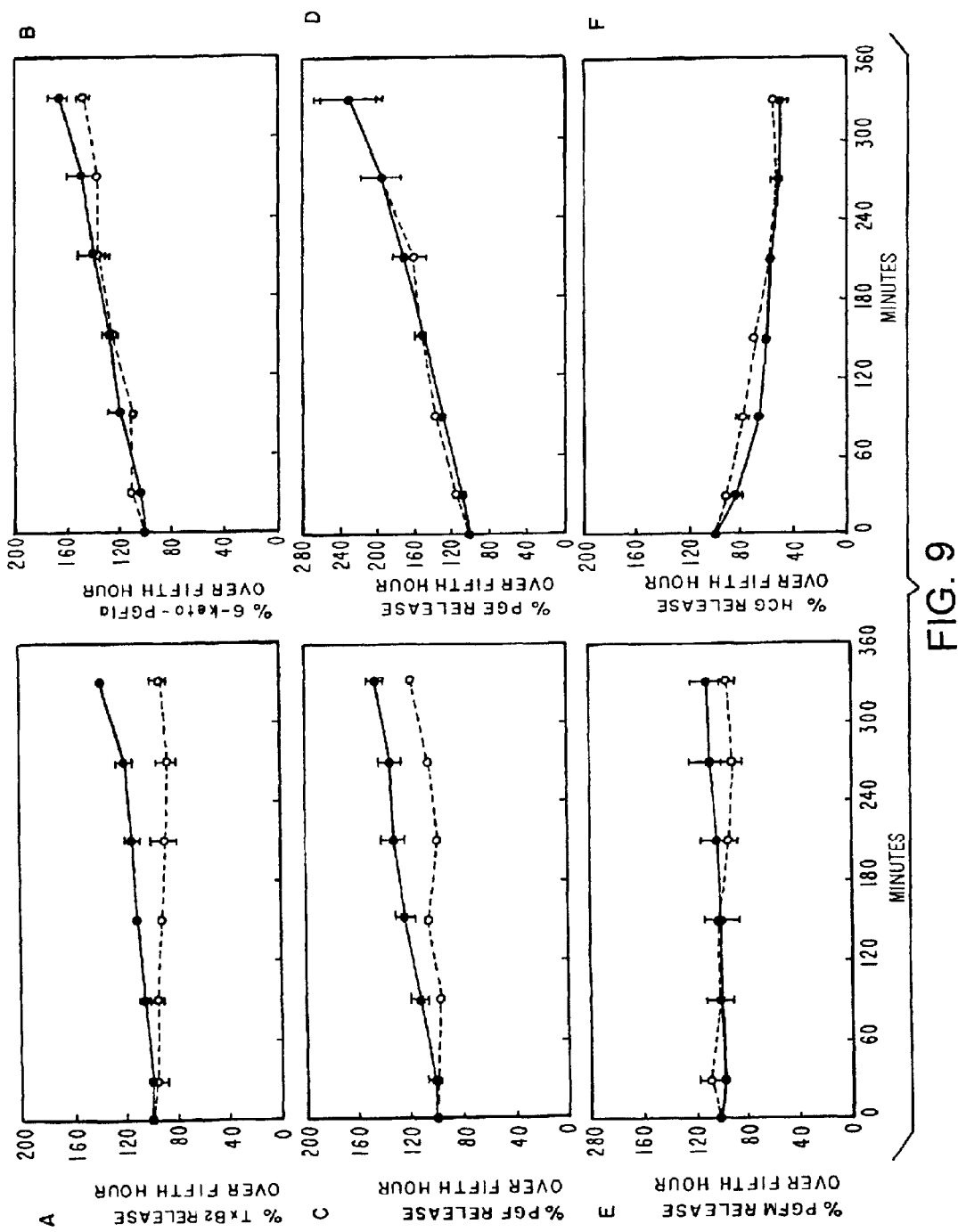
FIG. 9. The release (mean±SEM) of $TxB_2$, 6-keto-$PGF_{1\alpha}$, PGF, PGE, PGFM and hCG from replicate cultures of three different human term placentas throughout the 330 minutes of IGF-I treatment (■—■) or for controls (●—●) is shown. Significant difference are noted *P<0.05, **P<0.01.

The basal release (mean±SEM) of $TxB_2$, 6-keto-$PGF_{1\alpha}$, PGF and PGE, when normalized to the fifth-hour release, increased from the fifth to the tenth hour in culture 136%, 164%, 145% and 228%, respectively. However, the release of PGFM did not vary significantly during these hours of perifusion, whereas the release of hCG declined to 52% of the fifth-hour release during the following five hours. The release pattern between different placentas had an average coefficient of variation of only 6.5%, 11.6%, 9.5%, 12.2%, 18.0% and 8.9% for $TxB_2$, 6-keto-$PGF_{1\alpha}$, PGF, PGE, PGFM AND hCG, respectively, over the perifusion period. The solid lines in the graphs A–F of FIG. 9 illustrate the normalized release patterns (mean±SEM) for these prostanoids throughout the perifusion period.

The addition of IGF-I ($10^8$M) to the perifusing medium resulted in a highly significant ($P<0.003$) reduction of $TxB_2$ release (FIG. 9A). Normally, its release would increase about 1.6 times over control during the treatment period. However, exposure to IGF-I resulted in a significant inhibition of $TxB_2$ release by 150 minutes following treatment, decreasing to 85% of the control's release by the fifth hour of treatment.

The release of the prostacyclin metabolite, 6-keto-$PGF_{1\alpha}$, was not significantly altered by exposure for more than five hours to IGF-I (FIG. 9B). Its release continued to increase during the five hours, attaining 146% of the fifth-hour release.

However, the release of PGF was significantly ($P<0.01$) inhibited by IGF-I (FIG. 9C). This inhibition of PGF release was significant beginning from the third hour perifusion. By the fifth hour of treatment with IGF-I, the PGF release was 116%, which was not significantly different from the control's release. On the other hand, PGE, which also increased during the test period, was not affected by IGF-I (FIG. 9D). In the IGF-I treated tissues, the PGE increased to 228% of the fifth-hour release, as did the control tissues.

PGFM release was unchanged during the five hours of perifusion by the addition of IGF-I to the medium (FIG. 9E). As for the controls, PGFM did not increase throughout the perifusion.

The addition of IGF-I to the medium did not affect the release of the hCG as compared to the controls (FIG. 4F). HCG declined in the presence of IGF-I to 55% of the fifth-hour release, which was not significantly different from the control's release.

Figure 10:
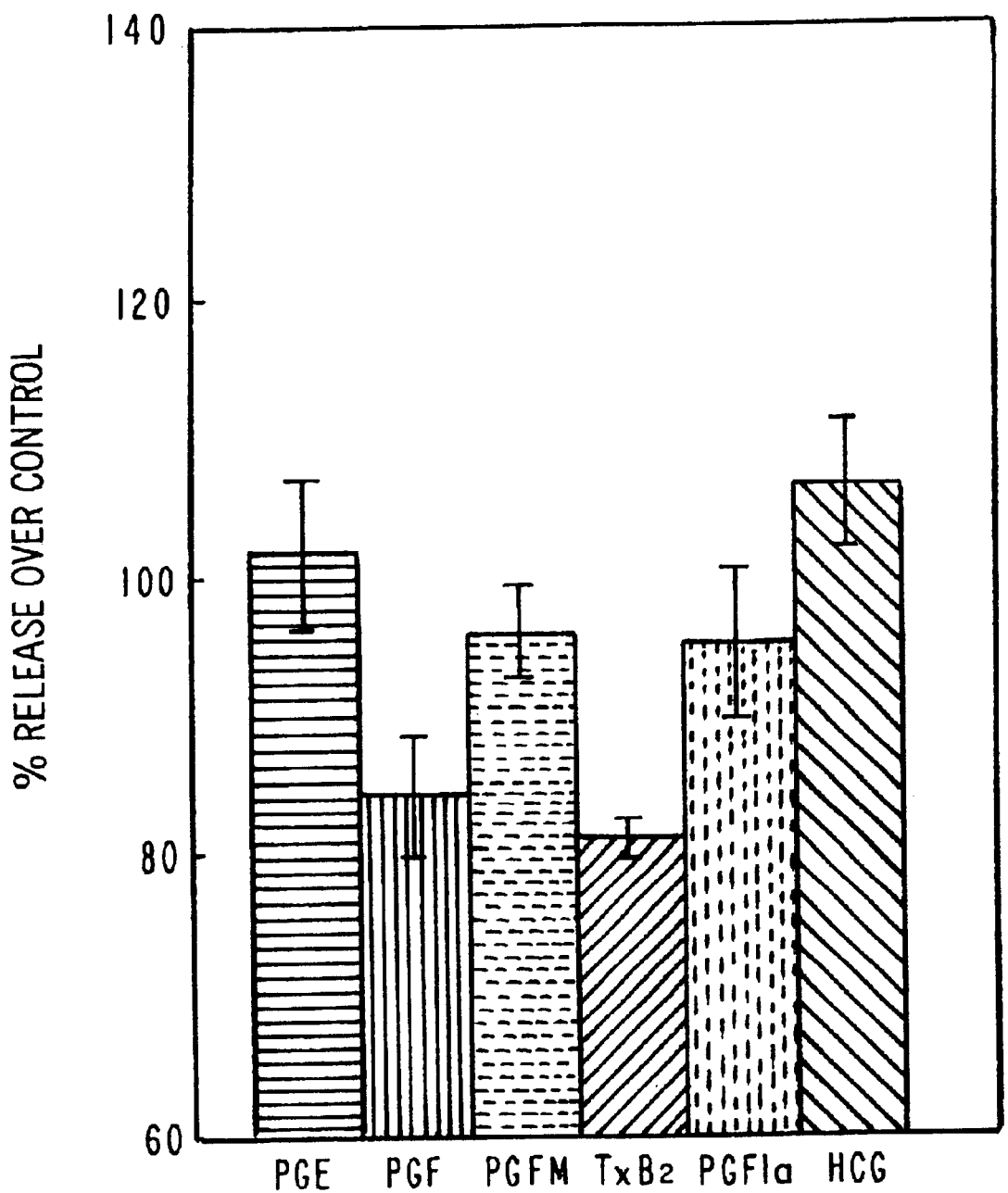
FIG. 10. The cumulative release for PGE, PGF, PGFM, $TxB_2$, 6-keto-$PGF_{1\alpha}$ and hCG for the IGF-I treatments from replicate explants of three different human term placentas as a percent of the controls' release is shown. Significant difference are noted, *P<0.05, **P<0.01.
Figure 11:
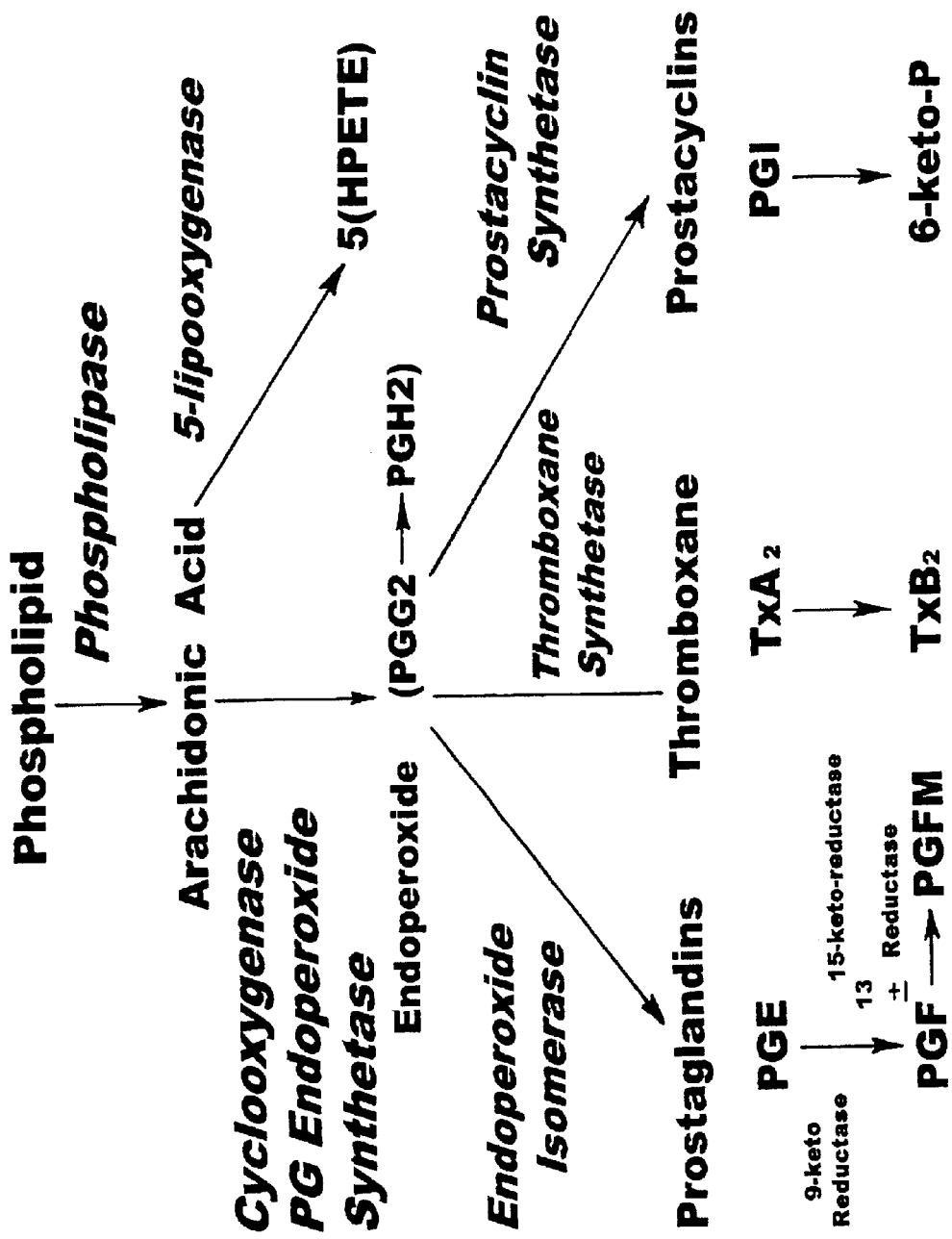
FIG. 11. Biosynthetic pathway of phospholipids to prostaglandins, thromboxane, and prostacyclins.

The cumulative release for each prostanoid and hCG in the presence of IGF-I is shown in FIG. 10. For each hormone, the cumulative release from the treated tissues was compared to cumulative release from the control tissues and expressed as the percent of the control. A significant reduction in PGF and $TxB_2$ releases (P<0.05 and 0.01, respectively) was observed with no significant change for the other hormones studied. Because both $TxB_2$ and PGF are vaso-constrictors, IGF-I may also act to enhance vasodilation in the placenta as well as to manage uterine contractility during labor.

EXAMPLE 7

Dose-Related Action of Insulin Like Growth Factor on Basal Thromboxane Production from Human Term Placenta The present example demonstrates that the inhibition of thromboxane $B_2$ production from placental cells by IGF-I is dose dependent. Dose related effects of IGF-I on human placental production of PGE, PGF, PGFM, and 6-keto-$PGF1\alpha$ is also demonstrated.

The dose-related effect of IGF-I on placental prostanoids was studied with the perifusion system previously described herein. Normal term deliveries were perifused with a defined Medium 199 containing no phenol red nor exogenous hormonal factors other than 100 $\mu$U/ml of insulin, estradiol (200 ng/ml), progesterone (4000 ng/ml) and dexamethasone ($10^{-8}$). These doses were chosen to emulate the normal term placental environment. Replicate chambers for the control (n=4) and treatment (n=3) explants for each placenta were made. Following a five-hour perifusion at 6 ml/hr with basal media, IGF-I (5, 10, 20, 40 or 80 ng/ml) was added to the triplicate chambers and sample collection continued every 30 minutes for another five hours. The average hormonal response for the replicate chambers of the control and the IGF-I treated explants was calculated and then the mean (±SEM) response for the different placentas with and without treatment was computed and the results compared. $TxB_2$ and PGF production were greatly reduced by IGF-I, whereas only a small reduction in PGE at a high dose of IGF-I was observed. $TxB_2$ was inhibited at even 10 ng/ml of IGF-I.

The basal release of thromboxane $B_2$ was relatively constant throughout the test period (i.e., 5th–10th hr. of placental perifusion). The addition of IGF-I at each dose indicated above resulted in the statistically significant inhibition of $TxB_2$ production. The magnitude of the inhibition was directly related to the dose of IGF-I, with $10^{-8}$M affecting the greatest inhibition—a 70% of the basal release.

These data demonstrate that IGF-I specifically inhibits vasoconstrictive prostanoid production by human placental explants in a dose-related manner, and that the active doses are well within a physiological range. Therefore, appropriate doses of IGF-I may be determined for human use in the inhibition of labor using standard pharmacological parameters known to those of skill in the art to provide the described inhibition of thromboxane and prostaglandin $F_{2\alpha}$ by placenta in vivo.

EXAMPLE 8

Use of IGF-I to Measure Placental Thromboxane Inhibition in a Biological Fluid Screening Assay The present invention may be employed in methods to measure thromboxane $B_2$ activity in a biological sample. The level of $TxB_2$ in biological fluids, i.e., blood, amniotic fluid, may also be used to evaluate the hormonal function of pregnancy and predict its outcome. Such information may indicate therapeutic treatment to effect normal levels and this appropriate regulate hormonal levels, leading to a better outcome of the pregnancy.

One of the demonstrated utilities of the inventive methods is to measure IGF-I induced inhibition of prostaglandin $F_{2\alpha}$ production by human placental cells, as demonstrated in the study of Example 6.

PROPHETIC EXAMPLE 9

Proposed Production of Antibodies Specific for Human Insulin Like Growth Factor The present example is provided to outline a method whereby antibodies having specific binding affinity for human IGF-I may be prepared for use as a specific inhibitor of IGF-I. The inhibitor of IGF-I may then be used as a pharmacological agent to reduce IGF-I levels in vivo, and eliminate Thromboxane inhibition and $PgF_{2\alpha}$ inhibition in a pregnant animal.

Balb/c mice may be immunized by intraperitoneal administration (ea. 100 mg each) of IGF-I by a standard dosage schedule sufficient to promote the production of anti-IGF-I antibodies in the animal. Mouse spleen cells from animals immunized with the IGF-I antigen may then be fused with P3K myeloma cells, or any immortal cancer cell, to form hybrid cells (hybridomas). The hybrid cells may then be plated and grown in HAT media.

Monoclonal antibody secreted in the media of cultures of the hybrid cells may then be collected. The monoclonal antibodies specific for IGF-I may then be employed as an inhibitor of IGF-I, thereby reducing IGF-I concentrations and reducing the potential of IGF-I mediated inhibition of thromboxane production and prostaglandin $F_{2\alpha}$ by human placental cells. These antibodies may also be formulated so as to be suitable for human use, and employed in the herein disclosed methods to induce labor, or at least to prevent the inhibition of labor, in a pregnant patient.

PROPHETIC EXAMPLE 10

Proposed use of Insulin Like Growth Factor-I to Affect a State of Pregnancy Insulin like growth factor-1 is a polypeptide hormone present in the intra-uterine tissue during pregnancy. IGF-I is shown in the present studies to be useful in regulating the production of intra-uterine prostanoids. The prostanoids thromboxane and prostaglandin F are both vasoconstrictors, and play a significant role in the regulation of intra-uterine blood flow and uterine contractility during pregnancy.

Vasoregulation in Pregnancy

As illustrated in FIGS. 4 and 5, IGF-I is effective in inhibiting thromboxane and prostaglandin F production by the placenta. Thus, by regulating the concentrations of intra-uterine IGF-I levels, either by altering its production, its metabolism or its activity, the production of thromboxane and prostaglandin F can be altered, leading either to increased or decreased vasoconstriction. Thus, increasing IGF-I may be used in inhibiting vasoconstriction. Therefore, IGF-I treatment could be used to inhibit intra-uterine vascular diseases in pregnancy through its affect on vasoconstrictive prostanoids.

The present methods may also be used in treating pregnancy induced hypertension, to reduce placental resistance, and to increase blood flow and thus nutrient flow to the fetus.

The activity of IGF-I in placental prostanoid production is a novel finding which may be therapeutically implemented to affect an appropriate vasoregulation in the pregnant animal and to promote adequate nutrient flow to the fetus.

Inhibiting Labor

As illustrated in FIGS. 4 and 5, IGF-I is effective in inhibiting placental prostaglandin F and thromboxane production by the placenta. Thus, by regulating the concentrations of intra-uterine IGF-I levels, either by altering its production, its metabolism, its binding proteins and/or its direct administration or inhibition, the production of $PGF_2$, and $TxB_2$ can be altered, leading either to increased or decreased vaso-constriction and/or uterine contractility as desired. Thus, increasing IGF-I may be used to inhibit labor or vaso-constriction. Therefore, IGF-I treatment could be used to inhibit labor through its affects on vasoconstriction prostanoids.

As part of a method for inhibitive labor in a pregnant human IGF-I may be injected intra-anionically (83 micrograms in 5 ml of 10 mM Hepes, 1 mM DTT, pH 7.4) into a pregnant animal having a gestational age of at least about 20 weeks, in humans. The standard dose to an average pregnant human female would be a dose sufficient to achieve a concentration of between 70 $\mu$g and 90 $\mu$g micrograms in the amniotic fluid or cord blood. For example, an intra-amniotic dose of between about 5 ng and 10 ng would be expected to provide such a concentration based on an average amniotic fluid volume of 1 liter. The most preferred mode of administration would therefore be intra-anionically to achieve sufficient concentrations. However, other routes of administration are contemplated to be equally efficacious. Such dose would be expected to inhibit labor in a treated pregnant human and would be employed to prevent premature termination of gestation in pregnant patients having a gestational age of between about 20–36 weeks.

Inducing Labor

According to one proposed embodiment, labor may be induced by inhibiting or reducing the concentrations of IGF-I in a pregnant animal. In humans, such a therapy would be desirable in females of greater than 40 weeks gestational age. Examples of inhibitors of IGF-I are antibodies having specific binding affinity for IGF-I, as described in Example 8. The most preferred mode of administration is contemplated to be by intra-amniotic injection or by intra-uterine vein administration. Other intravenous routes, as well as intramuscular administration, could also be employed.

Clinical treatment techniques well known to those of skill in the obstetrical arts would be used together with the disclosure of the present invention in either inducing or inhibiting labor, as well as in treating hypertension in the pregnant animal, according to the present invention.

The following references are specifically incorporated herein by reference in pertinent part for the purposes indicated herein and to demonstrate the state of the art.

BIBLIOGRAPHY

1. Angle M. J. & Johnston J. M., (1990), "Fetal tissues and autocoid biosynthesis in relation to the initiation of parturition and implantation," *In Uterine Function*, (Ed.) Carsten, M. E. & Miller, J. D. pp. 471–500, New York:Plenum Press.
2. Bala et al., (1990), Characterization of the major phosphoinositide-specific phospholipase-C of human anion, *Biology of Reproduction*, 43:704–711.
3. Challis J. R. G. & Vaughan, M. (1987), "Steroid synthetic and prostaglandin metabolizing activity is present in different cell populations from human fetal membranes and decidua," *American Journal of Obstetrics and Gynecology*, 157:1474–1481.
4. Demers, L. M & Gabbe, S. G. (1976), "Placental prostaglandin levels in preeclampsia," *American Journal of Obstetrics and Gynecology*, 126:137–139.
5. Duchesne et al., (1978), "Prostaglandin synthesis in human placenta and fetal membranes," *Prostaglandins*, 15:19–41.
6. Ekblad et al. (197), "The effect of acute hypoxia on prostaglandin release in perfused human fetal placenta," *Prostaglandins*, 33:553–560.
7. Gibbs et al. (1988), "Cyclo-oxygenase products formed by primary cultures of cells from human chorion laeve: Influence of steroids," *Canadian Journal of Physiology and Pharmacology*, 66:788–793.
8. Haning et al. (1982), "Effects of dibutyryl cAMP, LHRH, and aromatase inhibitor on simultaneous outputs of prostaglandin F2$\alpha$, and 13,14-dihydro-15-keto-prostaglandin F2$\alpha$ by term placental explants," *Prostaglandins*, 23:29–40.
9. Harper et al. (1983), "Prostaglandin production by human term placentas in vitro," *Prostaglandins Leukotrines and Medicine*, 11"121–129.
10. Hillier K. & Smith, M.D. (1981), "Prostaglandin E and F concentrations in placentae of normal, hypertensive and preeclamptic patients," *British Journal of Obstetrics and Gynaecology*, 88:274–277.
11. Jarabak J. (1972), "Human placental 15-hydroxy prostaglandin dehydrogenase," *Proceedings of the National Academy of Sciences USA*, 69:533–534.
12. Jogee et al. (1983), "Decreased prostacyclin production by placental cells in culture from pregnancies complicated by fetal growth retardation," *British Journal of Obstetrics and Gynaecology*, 90:247–250.
13. Kang et al. (1991), "Dose-related action of GnRH on basal prostanoid production from the human term placenta," *American Journal of Obstetrics and Gynecology*, 165:1771–1776.
14. Lytton F. D. & Mitchell M. D. (1988), "Phorbol ester-induced stimulation of prostaglandin biosynthesis in human anion cells," *Biochimica et Biophysica Acta*, 959:399–401.
15. Mitchell et al. (1978a), "Thromboxane $B_2$ and human parturition: Concentrations in the plasma and production in vitro," *Journal of Endocrinology*, 78:435–441.
16. Mitchell et al. (1978b), "Possible role for prostacyclin in human parturition," Prostaglandins, 16:931–937.
17. Mitchell et al. (1978c), "Specific production of prostaglandin E by human anion in vitro," *Prostaglandins*, 15:377–382.
18. Mitchell et al. (1982), "The human placenta: A major source of prostaglandin $D_2$," *Prostaglandins Leukotrines and Medicine*, 8:383–387.
19. Mitchell M. D. (1987), "Epidermal growth factor actions on arachidonic acid metabolism in human anion cells," *Biochimica et Biophysica Acta*, 928:240–242.
20. Mortimer et al. (1989), "The Distribution of pregnancy-associated prostaglandin synthetase inhibitor in the human placenta," *Journal of Pathology*, 159:239–243.
21. Myatt L. (1990), "Placental biosynthesis, metabolism, and transport of eicosanoids," In *Eicosanoids in Reproduction*, (Ed.) Mitchell, M. D. pp. 169–197, Boston: CRC Press.
22. Negro-Vilar et al. (1986), "Transmembrane signals mediating neural peptide secretion: Role of protein kinase C activators and arachidonic acid metabolites in luteinizing hormone-releasing hormone secretion," *Endocrinology*, 119:2796–2802.

23. Olson et al. (1983a), "Prostaglandin synthesis by human anion is dependent upon extracellular calcium," *Canadian Journal of Physiology and Pharmacology*, 61:1089–1092.
24. Olson et al. (1983b), "Estradiol-17β and 2-hydroxyestradiol-17β-induced differential production of prostaglandins by cells dispersed from human intrauterine tissues at parturition," *Prostaglandins*, 25:639–651.
25. Olson et al. (1983c), "Prostaglandin output in relation to parturition by cells dispersed from human intrauterine tissues," *Journal of Clinical Endocrinology and Metabolism*, 57:694–699.
26. Robinson et al. (1979), "The concentrations of the prostaglandins E and F, 13,14-dihydro-15-oxo prostaglandin F and Thromboxane $B_2$ in tissues obtained from women with and without preeclampsia," *Prostaglandins and Medicine*, 3:223–234.
27. Siler-Khodr et al. (1986a), "Differential inhibition of human placental prostaglandin release in vitro by a GnRH antagonist," *Prostaglandins*, 31:1003–1010.
28. Siler-Khodr et al. (1986b), "GnRH effects on placental hormones during gestation. III. Prostaglandin E, prostaglandin F, and 13,14-dihydro-15-keto-prostaglandin F," *Biology of Reproduction*, 35:312–319.
29. Siler-Khodr et al. (1986), "Gonadotropin-releasing hormone effects on placental hormones during gestation. I. Alpha-human chorionic gonadotropin, human chorionic gonadotropin and human chorionic somatomammotropin," *Biol. Reprod.*, 34:245–54.
30. Valenzuela G. & Bodhke R. R. (1980), "Effect of pregnancy-induced hypertension upon placental prostaglandin metabolism: decreased prostaglandin $F_{2\alpha}$ catabolism with normal prostaglandin $E_2$ catabolism," *American Journal of Obstetrics and Gynecology*, 136:255–256.
31. Vander et al. (1989), "Adenosine triphosphate activates the phospholipase-C cascade system in human anion cells without increasing prostaglandin production," *Endocrinology*, 124:2005–2012.
32. Walsh S. W. (1985), "Preeclampsi: an imbalance in placental prostacyclin and thromboxane production," *American Journal of Obstetrics and Gynecology*, 152:335–340.
33. Walsh et al. (1985), "Placental prostacyclin production in normal and toxemic pregnancies," *American Journal of Obstetrics and Gynecology*, 151:110–115.
34. Myatt et al. (1983), "Regulation of prostacyclin metabolism in human placental cells in culture by steroid hormones. In: Lewis P J et al., eds. Prostacyclin in pregnancy. New York: Raven Press, 119–29.
35. Walsh S. W. & Coulter S. (1989), "Increased placental progesterone may cause decreased placental prostacyclin production in preeclampsia," *Am J. Obstet. Gynecol.*, 161:1586–92.
36. E.P. 538342 (WO 92/00754).
37. Goodman and Gilmans (1990) Pharmacological Basis of Therapeutics, 8th Ed., Pergamon Press, pgs. 1–62, 933–953, 1332–1496, and 1640–1736.
38. Myatt L. Placental biosynthesis, metabolism, and transport of eicosanoids. In: Mitchell M D, ed. Eicosanoids in reproduction. Boca Raton: CRC Press; 1992–169–97.
39. Magness R R, Rosenfeld C R. Eicosanoids and the regulation of uteroplacental hemodynamics. In: Mitchell M D, ed. Eicosanoids in reproduction. Boca Raton: CRC Press, Inc., 1992–139–67.
40. Siler-Khodr T M, Khodr G S, Valenzuela G, Harber M J, Rhode J. GnRH effects on placental hormones during gestation. III. Prostaglandin E, prostaglandin F, and 13, 14-dihydro-15-keto-prostaglandin F. Biol Reprod (1986); 35:312–9.
41. Remingtons Pharmaceutical Sciences, 18th edition, Mack Publishing Company (1990) Easton, Pa., 18042.
42. Siler-Khodr T M, Khodr G S, Harper M J, Rhode J, Vickery B H, Nestor J J Jr. Differential inhibition of human placental prostaglandin release in vitro by a GnRH antagonist. Prostaglandins 1986;31:1003–10.
43. Kang I S, Koong M K, Forman J, Siler-Khodr T M. Dose-related action of gonadotropin-releasing hormone on basal prostanoid production from the human term placenta. Am J Obstet Gynecol 1991;165:1771–6.
44. Walsh S W, Parisi V M. Eicosanoids and hypertension in pregnancy. In: Mitchell M D, ed. Eicosanoids in reproduction. Boca Raton: CRC Press, 1992:249–72.
45. Makila U M, Viinikka L, Ylikorkala O. Increased thromboxane $A_2$ production but normal prostacyclin by the placenta in hypertensive pregnancies. Prostaglandins 1984;27:87–95.
46. Walsh S W. Preeclampsia: an imbalance in placental prostacyclin and thromboxane production. Am J Obstet Gynecol 1985; 152:335–40.
47. Walsh S. Progesterone and estradiol production by normal and preeclamptic placentas. Obstet Gynecol 1988;71:222–6.
48. Smith S K, Kelly R W. The effect of the antiprogestins RU 486 and ZK 98734 on the synthesis and metabolism of prostaglandins $F_{2\alpha}$ and $E_2$ in separated cells from early human decidua. J Clin Endocrinol Metab 1987;65:527–34.
49. Ahmed N A, Murphy B E. The effects of various hormones on human chorionic gonadotropin production in early and late placental explant cultures. Am J Obstet Gynecol. 1988;159:1220–7.
50. Iwashita M, Watanabe M, Adachi T, et al. Effect of gonadal steroids on gonadotropin-releasing hormone-stimulated human chorionic gonadotropin release by trophoblast cells. Placenta 1989;10:103–12.
51. Siler-Khodr T M, Khodr G S, Rhode J, Vickery, B H, Nestor J J Jr. Gestational age-related inhibition of placental hCG, hCG and steroid hormone release in vitro by a GnRH antagonist. Placenta 1987;8:1–114.
52. Siler-Khodr T M, Khodr G S, Valenzuela G, Rhode J. Gonadotropin-releasing hormone effects on placental hormones during gestation. II. Progesterone, estrone, estradiol and estriol. Biol Reprod 1986;24:255–64.
53. Nestler J E. Insulin and insulin-like growth factor-I stimulate the 3-beta-hydroxysteroid dehydrogenase activity of human placental cytotrophoblasts. Exp Biol Med 1989;125:2127–33.
54. Nestler J E, Williams T. Modulation of aromatase and P450 cholesterol side-chain cleavage enzyme activities of human placental cytotrophoblast by insulin and insulin-like growth factor I. Endocrinology 1987;121–1845–52.
55. Iwashita M, Watanabe M, Setoyama M, et al. Effects of diacylglycerol and gonadotropin-releasing hormone on human chorionic gonadotropin release by cultured trophoblast cells. Placenta 1992; 13:213–21.

What is claimed is:

1. A method for regulating placental cell production of thromboxane and $PGF_{2\alpha}$ comprising treating placental cells with a pharmacologically effective amount of insulin-like growth factor I sufficient to inhibit thromboxane and prostaglandin $F_{2\alpha}$ production without affecting prostacyclin or prostaglandin $E_2$ production.

2. The method of claim 1 wherein placental production of human chorionic gonadotropin and PGFM is not affected.

3. The method of claim 1 wherein the placental cells are human placental cells.

4. The method of claim 1 wherein the pharmacologically effective concentration of insulin like growth factor is between about $10^{-7}$ to about $10^{-10}$.

5. A method for inhibiting labor by inhibiting the production of prostaglandin $F_{2\alpha}$ and thromboxane by chorionic tissue comprising administering to a pregnant animal a pharmacologically effective amount of insulin like growth factor I or an analog thereof sufficient to inhibit the production of thromboxane and prostaglandin $F_{2\alpha}$ by placental cells without affecting prostacyclin, PGE, PGFM and human chorionic gonadotropin production.

6. The method of claim 5 wherein the placental cells are human placental cells.

7. The method of claim 5 wherein the insulin like growth factor is insulin like growth factor-I and wherein the pharmacologically effective amount of insulin like growth factor is an amount effective to achieve a concentration of between about 5 ng/ml to about 80 ng/ml in the amniotic fluid or cord blood of the pregnant animal.

8. The method of claim 5 wherein the insulin like growth factor is administered subcutaneously, intramuscularly, intravenously or intra-amniotically.

9. The method of claim 5 wherein the insulin like growth factor is administered in a pharmacologically acceptable carrier solution.

10. The method of claim 5 wherein the pregnant animal is a human.

* * * * *